US008362086B2

(12) United States Patent
Soll et al.

(10) Patent No.: US 8,362,086 B2
(45) Date of Patent: Jan. 29, 2013

(54) LONG ACTING INJECTABLE FORMULATIONS

(75) Inventors: Mark D. Soll, Alpharetta, GA (US);
Peter Hanson, Suwanee, GA (US);
Krishan Kumar, Manalapan, NJ (US);
Monica Tejwani-Motwani, Somerset, NJ (US)

(73) Assignee: Merial Limited, Duluth, GA (US)

( * ) Notice: Subject to any disclaimer, the term of this patent is extended or adjusted under 35 U.S.C. 154(b) by 730 days.

(21) Appl. No.: 11/207,980

(22) Filed: Aug. 19, 2005

(65) Prior Publication Data
US 2007/0042013 A1 Feb. 22, 2007

(51) Int. Cl.
*A61K 31/63* (2006.01)
*A61K 31/7048* (2006.01)

(52) U.S. Cl. ............... 514/603; 514/28; 514/460

(58) Field of Classification Search .......... 424/405; 514/28
See application file for complete search history.

(56) References Cited

U.S. PATENT DOCUMENTS

| 5,773,422 | A | * | 6/1998 | Komer | 514/30 |
| 6,733,767 | B2 | * | 5/2004 | Chern et al. | 424/426 |
| 2002/0064547 | A1 | | 5/2002 | Chern et al. | |

FOREIGN PATENT DOCUMENTS

| EP | 0125004 A1 | 11/1984 |
| EP | 0537559 A1 | 4/1993 |
| EP | 1484033 A1 | 12/2004 |
| WO | WO9505812 A1 | 3/1995 |
| WO | WO03072112 A1 | 9/2003 |
| WO | WO2004028272 A2 | 4/2004 |

OTHER PUBLICATIONS

Loyacano et al. Effects of parenteral administration of doramectin or a combination of ivermectin and clorsulon on control of gastrointestinal nematode and liver fluke infections and on growth performance in cattle, JAVMA, vol. 218, No. 9, May 1, 2001.*
Montana Youth Livestock Quality Assurance, http://www.falloncounty.net/extension/FourH/MTYouthLivestockQuality.pdf accessed Dec. 13, 2008.*
Pharmaceutical Dosage Forms and Drug Delivery Systems 7th edition, Ansel et al., Lippincott Williams and Wilkins, 1999, p. 88.*
http://www.yashicapharma.com/clorsulon.html accessed Mar. 31, 2010.*
Martinez-Asencio et al. Tetrahedron Letters, 2010, vol. 51, pp. 325-327.*
Meaney et al. Parasitol. Res., 2003, vol. 91, pp. 238-250.*
Borges FA, Cho HS, Santos E, Oliveira GP, Costa AJ. Pharmacokinetics of a new long acting endectocide formulation containing 2.25% ivermectin and 1.25% abamectin in cattle. J Vet Pharmacol Ther. Feb. 2007;30(1):62-7.

* cited by examiner

*Primary Examiner* — James D Anderson
(74) *Attorney, Agent, or Firm* — Judy Jarecki-Black; John Ezcurra; Merial Limited

(57) ABSTRACT

The application relates to long acting injectable (LAI) formulations for combating ectoparasites and endoparasites in mammals. In particular, this invention provides for a LAI formulation comprising a subcutaneously volatile solvent, a biologically acceptable polymer, a bioactive agents and optionally one or more anti-ectoparasitically or anti-endoparasitically acceptable additive or excipient. Surprisingly, the liquid long acting injectable formulations of the invention solve the problems associates with previous injectable formulations by having long term stability, being able to accommodate smaller needle diameters and achieving long acting effects in the control of pests in a mammal. The unique formulations of the invention also allow for combating ectoparasites and endoparasites which have become resistant to macrolide antibiotics.

12 Claims, 9 Drawing Sheets

Figure 1 - Eprinomectin Plasma Levels after Injection Behind the Ear of Cattle

Figure 2 - Mean Plasma Concentrations of Eprinomectin Following Administration of 1 mg/kg Eprinomectin Long Acting Injectable Formulation in the Right Neck in front of the Shoulder of Cattle Figure 3 - Mean Plasma Concentrations of Eprinomectin Following Administration of 1 mg/kg Eprinomectin Long Acting Injectable Formulation in the Left Shoulder of the Cattle Error bars are ± standard deviation Figure 4 - Mean Plasma Concentration of Eprinomectin Following Administration of 1 mg/kg of Eprinomectin Long Acting Injectable Formulations in the Ear or Shoulder of Cattle Figure 7 - Plasma Depletion of Eprinomectin in Sheep

LONG ACTING INJECTABLE FORMULATIONS

INCORPORATION BY REFERENCE

Mention is made of U.S. Pat. No. 6,733,767 entitled "Liquid Polymeric Compositions for Controlled Release of Bioactive Substances" which is hereby incorporated by reference.

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

This application relates to long acting injectable (LAI) formulations for combating ectoparasites and endoparasites in mammals. In particular, this invention provides for a LAI formulation comprising a subcutaneously volatile solvent or mixtures thereof, a biologically acceptable polymer, bioactive agents including optionally one and/or more anti-ectoparasitically or anti-endoparasitically acceptable additive or excipient and optionally an antioxidant.

BACKGROUND OF THE INVENTION

The bioactive agents which are used in the inventive formulations are well known to the practitioner to which this invention pertains. Classes of bioactive agents contemplated by the inventive antibiotic formulations include anthelmintics, insecticides, acaricides, parasiticides, growth enhancers, and nonsteroidal anti-inflammatory drugs (NSAIDS). Specific classes of compounds which fall within these classes of bioactive agents include, for example, avermectins, milbemycins, nodulisporic acid and its derivatives, estrogens, progestins, androgens, substituted pyridylmethyl derivatives, phenylpyrazoles, and COX-2 inhibitors.

The avermectin and milbemycin series of compounds are potent anthelmintic and antiparasitic agents against a wide range of internal and external parasites. The compounds which belong to this series are either natural products or are semi-synthetic derivatives thereof. The structure of these two series of compounds are closely related and they both share a complex 16-membered macrocyclic lactone ring; however, the milbemycins do not contain the disaccharide substitutent in the 13-position of the lactone ring. The natural product avermectins are disclosed in U.S. Pat. No. 4,310,519 to Albers-Schonberg, et al., and the 22,23-dihydro avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, N.Y. (1989). Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, N.J. (1996). Semi-synthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, and 4,920,148.

European Patent Application 413,538 relates to an injectable formulation containing an avermectin compound and triacetin. European Patent Application 535,734 relates to an injectable formulation containing an avermectin compound and hydrogenated castor oil in a hydrophobic carrier such as triacetin. The formulations in both European Patent Applications are said to provide efficacy against external and internal parasites in animals only for up to 42 days. Neither of these applications suggests or teaches how to manipulate the composition of the formulation in order to achieve efficacy beyond 42 days.

Nodulisporic acid and its derivatives are a class of acaricidal, antiparasitic, insecticidal and anthelminitic agents known to a practitioner of the art. These compounds are used to treat or prevent infections in humans and animals. These compounds are described, for example, in U.S. Pat. No. 5,399,582 and WO 96/29073. Additionally, the compounds can be administered in combination with other insecticides, parasiticides, and acaricides. Such combinations include anthelminitic agents, such as those discussed above which include abamectin, doramectin, emamectin, eprinomectin, ivermectin, latidectin, lepimectin and selamectin, as well as other agents such as thiabendazole, febantel or morantel; phenylpyrazoles such as fipronil; and insect growth regulators such as lufenuron. Such combinations are also contemplated in the present invention.

Generally, all classes of insecticides are provided for in this invention. One example of this class include substituted pyridylmethyl derivatives such as imidacloprid. Agents of this class are described, for example, in U.S. Pat. No. 4,742,060 or in EP 892,060. It would be well within the skill level of the practitioner to decide which individual compound can be used in the inventive formulation to treat a particular infection of an insect.

Phenylpyrazoles are another class of insecticides which possess excellent insecticidal activity against all insect pests including blood-sucking pests such as ticks, fleas etc., which are parasites on animals. This class of agents kills insects by acting on the gamma-butyric acid receptor of invertebrates. Such agents are described, for example, in U.S. Pat. Nos. 5,567,429, 5,122,530, and EP 295,117. It would be well within the skill level of the practitioner to decide which individual compounds can be used in the inventive formulations.

Insect growth regulators are another class of insecticides or acaricides, which are also provided for in the inventive formulations. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356; 3,818,047; 4,225,598; 4,798,837; 4,751,225, as well as in EP 179,022 or U.K. 2,140,010. Again, it would be well within the skill level of the practitioner to decide which individual compounds can be used in the inventive formulation.

Estrogens, progestins, and androgens refers to classes of chemical compounds which are also well known to a practitioner in this art. In fact, estrogens and progestins are among the most widely prescribed drugs and are used, for example, alone or in combination for contraception or hormone replacement therapy in post menopausal women. Estrogens and progestins occur naturally or are prepared synthetically. This class of compounds also includes estrogens or progesterone receptor antagonists. Antiestrogens, such as tamoxifen and clomiphene, are used to treat breast cancer and infertility.

Antiprogestives are used as contraceptives and anticancer drugs, as well as to induce labor or terminate a pregnancy.

The androgens and antiandrogens structurally related to the estrogens and progestins as they are also biosynthesized from cholesterol. These compounds are based on testosterone. Androgens are used for hypogonadism and promote muscle development. Antiandrogens are used, for example, in the management of hyperplasia and carcinoma of the prostate, acne, and male pattern baldness as well as in the inhibition of the sex drive in men who are sex offenders. Estrogen, progestins, and androgens are described, for example, in "Goodman & Gilman's The Pharmacological Basis of Therapeutics," 10th ed., J. G. Hardman and Limbird, eds., Chapters 58 and 59, pp. 1597-1648, McGraw-Hill, N.Y. (2001) or in "Principles of Medicinal Chemistry," ed., W. O. Foye, ed., Ch. 21, pp. 433-480, Lea & Febiger, Philadelphia (1989).

Estrogens, progestins and androgens are also used in animal husbandry as growth promoters for food animals. It is known in the art that compounds of these classes act as growth-promoting steroids in animals such as cattle, sheep, pigs, fowl, rabbits, etc. Delivery systems to promote the growth of animals are described, for example, in U.S. Pat. Nos. 5,401,507, 5,288,469, 4,758,435, 4,686,092, 5,072,716 and 5,419,910.

NSAIDS are well known in the art. The classes of compounds which belong to this group include salicylic acid derivatives, para-aminophenol derivatives, indole and indene acetic acids, heteroaryl acetic acids, arylpropionic acids, anthranilic acids (fenamates), enolic acids, and alkanones. NSAIDS exert their activity by interfering with prostaglandin biosynthesis by irreversibly or reversibly inhibiting cycloxygenase. Also included are COX-2 inhibitors which act by inhibiting the COX-2 receptor. Compounds of this group possess analgesic, antipyretic and nonsteroidal anti-inflammatory properties. Compounds belonging to these classes are described, for example, in Chapter 27 of Goodman and Gilman on pages 687-731 or in Chapter 22 of Foye on pages 503-530 as well as in U.S. Pat. Nos. 3,896,145; 3,337,570; 3,904,682; 4,009,197; 4,223,299; and 2,562,830, as well as the specific agents listed in The Merck Index.

While the individual bioactive agents are well-known in the art, there has been difficulties in the art to provide for a viable, easy to use, long acting injectable formulation containing these bioactive agents. Particularly problematic is the use of biologically acceptable polymers (e.g. poly(lactic-co-glycolic)acid copolymer (PLGA)) for injectable formulations which are useful for inducing long term release of the bioactive agent.

European Patent Application 0537559 concerns polymeric compositions having a thermoplastic polymer, rate modifying agent, water soluble bioactive material and water-miscible organic solvent. Upon exposure to an aqueous environment (e.g. body fluids) the liquid composition is capable of forming a biodegradable microporous, solid polymer matrix for controlled release of water soluble or dispersible bioactive materials over about four weeks. The thermoplastic polymer may be, among many listed, polylactide, polyglycolide, polycaprolactone or copolymers thereof, and is used in high concentration (45 to 50%). The rate modifying agent may be, among many others listed, glycerol triacetate (triacetin); however, only ethyl heptanoate is exemplified; and the amount of the rate modifying agent is no more than 15%. Indeed, with respect to the patent literature, reference is made to:

| | |
|---|---|
| 4,150,108 | Graham |
| 4,329,332 | Couvreur et al. |
| 4,331,652 | Ludwig et al. |
| 4,333,919 | Kleber et al. |
| 4,389,330 | Tice et al. |
| 4,489,055 | Couvreur et al. |
| 4,526,938 | Churchill et al. |
| 4,530,840 | Tice et al. |
| 4,542,025 | Tice et al. |
| 4,563,489 | Urist |
| 4,675,189 | Kent et al. |
| 4,677,191 | Tanaka et al. |
| 4,683,288 | Tanaka et al. |
| 4,758,435 | Schaaf |
| 4,857,335 | Bohm |
| 4,931,287 | Bae et al. |
| 5,178,872 | Ohtsubo et al. |
| 5,252,701 | Jarrett et al. |
| 5,275,820 | Chang |
| 5,478,564 | Wantier et al. |
| 5,540,912 | Roorda et al. |
| 5,447,725 | Damani et al. |
| 5,599,852 | Scopelianos et al. |
| 5,607,686 | Totakura et al. |
| 5,609,886 | Wantier et al. |
| 5,631,015 | Bezwada et al. |
| 5,654,010 | Herbert et al. |
| 5,700,485 | Johnson et al. |
| 5,702,717 | Berde et al. |
| 5,711,968 | Tracy et al. |
| 5,733,566 | Lewis |
| 4,938,763 | Dunn et al. |
| 5,077,049 | Dunn et al. |
| 5,278,201 | Dunn et al. |
| 5,278,202 | Dunn et al. |
| 5,288,496 | Lewis |
| 5,324,519 | Dunn et al. |
| 5,324,520 | Dunn et al. |
| 5,340,849 | Dunn et al. |
| 5,368,859 | Dunn et al. |
| 5,401,507 | Lewis |
| 5,419,910 | Lewis |
| 5,427,796 | Lewis |
| 5,487,897 | Polson et al. |
| 5,599,552 | Dunn et al. |
| 5,632,727 | Tipton et al. |
| 5,643,595 | Lewis |
| 5,660,849 | Polson et al. |
| 5,686,092 | Lewis et al. |
| 5,702,716 | Dunn et al. |
| 5,707,647 | Dunn et al. |
| 5,717,030 | Dunn et al. |
| 5,725,491 | Tipton et al. |
| 5,733,950 | Dunn et al. |
| 5,736,152 | Dunn et al. |
| 5,744,153 | Yewey et al. |
| 5,759,563 | Yewey et al. |
| 5,780,044 | Yewey et al. |

These documents tend to provide compositions that form a solid, gel or coagulated mass; for instance, a significant amount of polymer is contemplated in these documents, akin to European Patent Application 0537559, which makes them wholly unsuitable for injectable formulations.

Shah et al (J. Controlled Release, 1993, 27:139-147), as relating to formulations for sustained release of bioactive compounds containing various concentrations of poly (lactic-co-glycolic)acid copolymer (PLGA) dissolved in vehicles such as triacetin; Lambert and Peck (J. Controlled Release, 1995, 33:189-195), as a study of the release of protein from a 20% PLGA solution in N-methylpyrrolidone exposed to aqueous fluid; and Shivley et al (J. Controlled Release, 1995, 33:237-243), as a study of the solubility parameter of poly (lactide-co-glycolide)copolymer in a variety of solvents, and the in vivo release of naltrexone from two injectable implants (5% naltrexone in either 57% PLGA and 38% N-methylpyrrolidone or 35% PLGA and 60% N-methylpyrrolidone).

Controlled release of hydrophobic bioactive substance in vivo over an extended period of time is referred to in U.S. Pat. No. 6,733,767 which includes a polymer such as PLGA with a mixture of hydrophilic and lipophilic solvents. However, these formulations also suffer from problems of long term shelf stability and also with plugging of the needles used to inject the formulation.

An additional problem in the art is that some strains of ectoparasites and endoparasites have become resistant to antiparasitic agents administered in conventional formulations rendering them unsuitable for combating ectoparasites and endoparasites.

There is still a need in the art for long acting formulations which are suitable for injection and which have long term shelf stability. In addition, an ideal injectable formulation would not only be usable with smaller needle diameters but would have a long acting effect that would have a season long effect during the breeding perior for livestock mammals such as cattle, sheep and pigs or minimize the number of injections when applying to domestic mammals such as dogs and cats. It would also be beneficial if formulations could be developed which are able to treat ectoparasites and endoparasites which have become resistant to antiparasitic agents including macrocyclic lactones.

Citation or identification of any document in this application is not an admission that such document is available as prior art to the present invention.

SUMMARY OF THE INVENTION

An object of the invention is to provide a liquid long acting injectable formulation for combating ectoparasites and/or endoparasites. This object is achieved by formulations which comprise:
(a) a therapeutically effective amount of a bioactive agent;
(b) a subcutaneously volatile solvent or mixture of subcutaneously volatile solvents;
(c) a biologically acceptable polymer;
(d) optionally, at least one anti-ectoparasitically or anti-endoparasitically acceptable additive, excipient or mixtures thereof; and
(e) optionally, an antioxidant.

Surprisingly, the liquid long acting injectable formulations of the invention solve the problems associated with previous injectable formulations by having long term stability in a liquid form thereby being able to accommodate smaller needle diameters and providing a convenient dosage form for achieving long acting effects in the control of pests in a mammal. The unique formulations of the invention also allow for combating ectoparasites and endoparasites which have become resistant to antiparasitic agents administered in a standard dosage form.

While not wishing to be bound by any particular theory, it is believed that the beneficial effects of the invention occur because the subcutaneously volatile solvent is able to sufficiently dissolve the biologically acceptable polymer and bioactive agent keeping it in solution prior to injection. However, upon injection of the formulation, the subcutaneously volatile solvent dissipates and allows for better distribution within the matrix of the biologically acceptable polymer which in turn allows for better release of the bioactive agent over longer periods of time than previously achievable.

For the purposes of this application, the term "season long" defines a time period which is at least about 4 months up to about one year. The term "month" as used in this application is equivalent to about 30 days and "one year" is equivalent to about 365 days.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
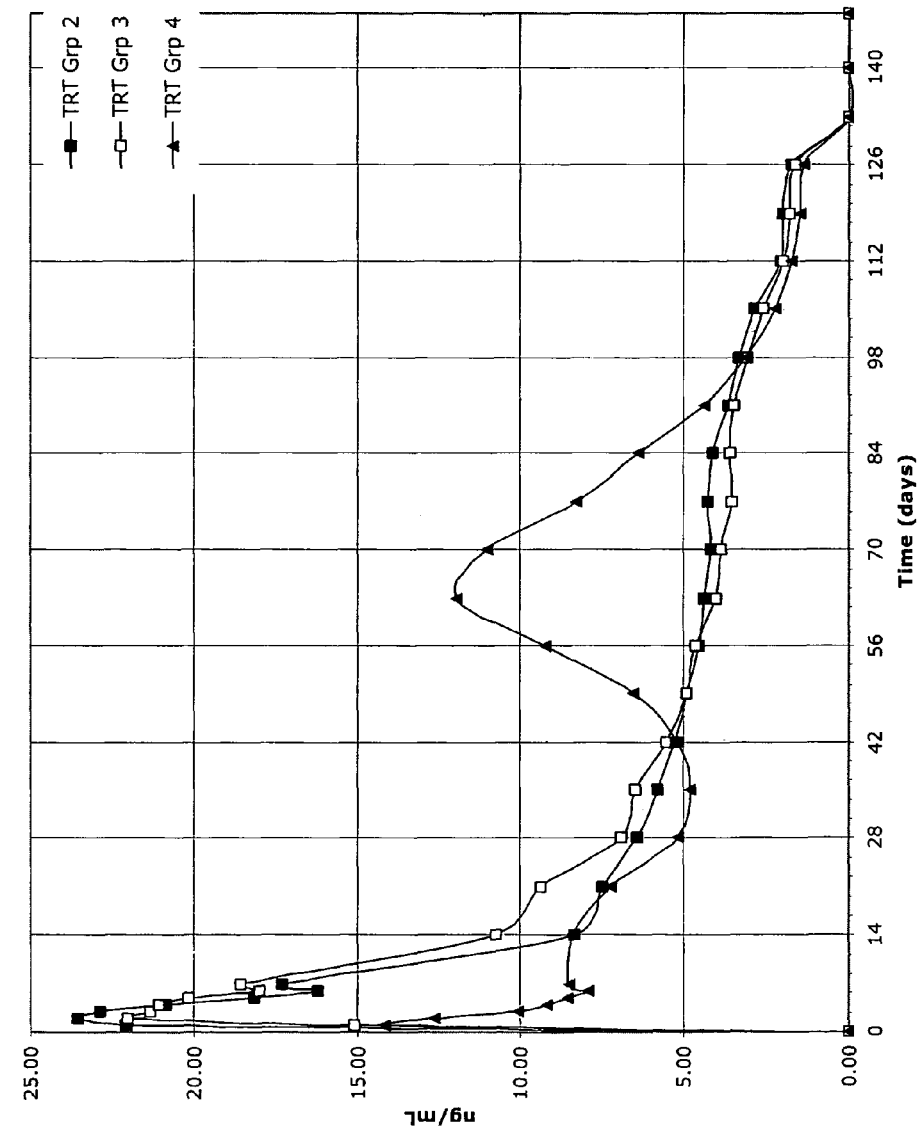
FIG. 1 shows the mean eprinomectin plasma level after injecting the long acting injectable formulation behind the ear of cattle.
Figure 2:
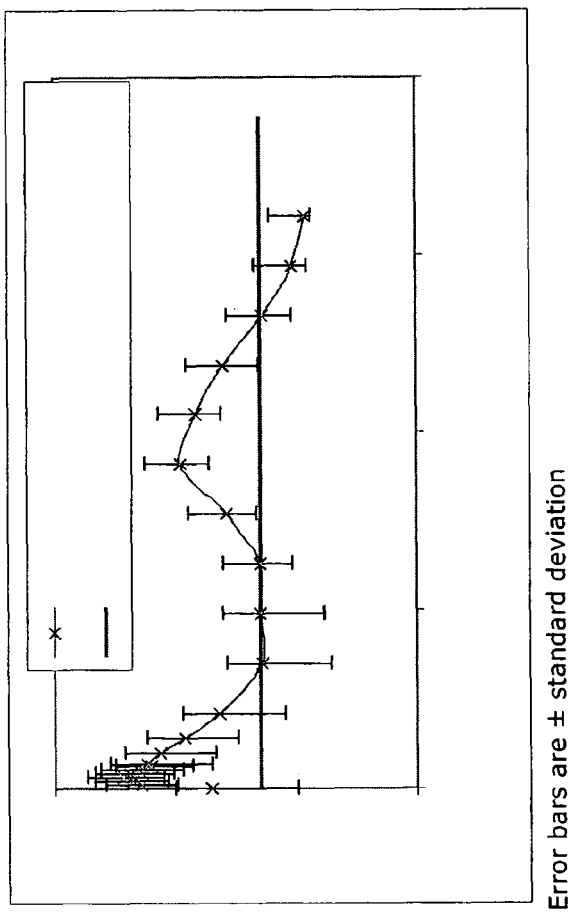
FIG. 2 shows the mean eprinomectin plasma level after injecting the long acting injectable formulation in the right neck in front of the shoulder of cattle
Figure 3:
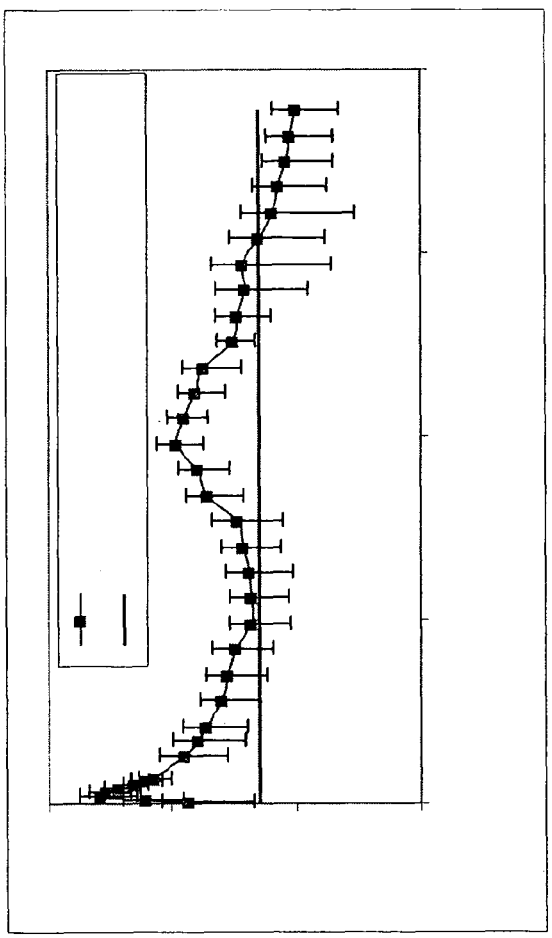
FIG. 3 shows the mean eprinomectin plasma level after injecting the long acting injectable formulation in the left shoulder of cattle

One embodiment of the invention is a liquid long acting injectable formulation for combating ectoparasites and/or endoparasites which comprise:
(a) a therapeutically effective amount of at least one bioactive agent;
(b) a subcutaneously volatile solvent or mixture of subcutaneously volatile solvents;
(c) a biologically acceptable polymer;
(d) optionally, at least one anti-ectoparasitically or anti-endoparasitically acceptable additive, excipient or mixtures thereof; and
(e) optionally, an antioxidant.

A further embodiment of the liquid long acting injectable formulation is a formulation which comprise:
(a) the bioactive agent is selected from the group consisting of avermectins milbemycins, derivatives thereof and mixtures thereof;
(b) the subcutaneously volatile solvent is selected from the group consisting of alcohols, ketones, ethers, esters, amides and mixtures thereof;
(c) the biologically acceptable polymer is selected from the group consisting of polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malicacid), poly(amino acids), poly(methyl vinyl ether), poly(maleic anhydride), chitin, chitosan, and copolymers, terpolymers, and mixtures thereof;

(d) optionally, at least one anti-ectoparasitically or anti-endoparasitically acceptable additive, excipient or mixtures thereof; and (e) optionally, an antioxidant.

A still further embodiment of the liquid long acting injectable formulation is a formulation which comprise:

(a) the bioactive agent is selected from the group consisting of abamectin, doramectin, emamectin, eprinomectin, ivermectin, latidectin, lepimectin, and selamectin, milbemectin, milbemycin D, milbemycin oxime moxidectin and mixtures thereof;

(b) the subcutaneously volatile solvent is selected from the group consisting of ethanol, 1-propanol, 2-propanol, 1-butanol, 2-butanol, 1-pentanol, 2-pentanol, 3-pentanol, propylene glycol, PEG 200, PEG 300, PEG 400, diethylene glycol ethyl ether, isopropylidene glycerol, dimethyl isosorbide, propylene carbonate, glycerol, acetone, N-methyl-pyrrolidone, N-pyrrolidone, methylethylketone (MEK), dimethylsulfoxide (DMSO), 1-dodecylazacycloheptane, dipropyleneglycol methyl ether, methyl acetate, ethyl acetate, ethyl lactate, dimethylformamide, N,N-diethyl-m-toluamide, dimethylacetamide, ethylacetamide, tetrahydrofuran, caprolactam, decylmethylsulfoxide, triacetin, solketal, propylene carbonate, ethyl lactate and mixtures thereof;

(c) the biologically acceptable polymer is selected from the group consisting of polylactides, polycaprolactones, polyglycolides and copolymers thereof.

A yet further embodiment of the liquid long acting injectable formulation is a formulation which comprise:

(a) the bioactive agent is selected from the group consisting of emamectin, eprinomectin, ivermectin, moxidectin and mixtures thereof;

(b) the subcutaneously volatile solvent is selected from the group consisting of glycerol formal, N-methylpyrrolidone (NMP), triacetin, dimethylacetamide, ethylacetamide, solketal, propylene carbonate, ethyl lactate, ethyl acetate, and mixtures thereof;

(c) the biologically acceptable polymer is poly(lactic-co-glycolic) acid copolymer (PLGA).

In another embodiment of the invention, the formulation of the invention is for combatting endoparasites wherein the endoparasite is a helminth selected from the group consisting of *Ancylostoma, Anecator, Ascaris, Capillaria, Cooperia, Dirofilaria, Dictyocaulus, Echinococcus, Fasciola, Haemonchus, Oesophagostomum, Ostertagia, Toxocara, Strongyloides, Toxascaris, Trichinella, Trichuris, Trichostrongylus* and mixtures thereof.

In a further embodiment of the formulation for combating ectoparasites, the ectoparasite is an insect or arachnid including those of the genera *Ctenocephalides, Rhipicephalus, Dermacentor, Ixodes, Boophilus, Ambylomma, Hyalomma, Sarcoptes, Psoroptes, Otodectes, Chorioptes, Hypoderma, Damalinia, Linognathus, Hematopinus, Solenoptes* and mixtures thereof.

In another embodiment of invention, the formulation of the invention has a therapeutic effect for a period of time selected from the group consisting of at least about four months to about one year, at least about four months to about six months and at least about four months to about five months.

Another embodiment of the invention is directed to a process of making the liquid long acting injectable formulation of the invention which comprises:

(i) dissolving the biologically acceptable polymer in a subcutaneously volatile solvent to form a solution;

(ii) adding a therapeutically effective amount of a bioactive agent to the solution to form the formulation.

In a further embodiment of the invention directed to the process of making the liquid long acting injectable formulation of the invention, the liquid long acting injectable formulation is free of particles which plug the needle used for injection wherein the needle gauge is selection from the group consisting of about 18 to about 30, about 18 to about 24 and about 24 to about 30.

Another embodiment of the invention is directed toward the method of combating ectoparasites and/or endoparasites in a mammal which comprises of parenteral administration of a therapeutically effective amount of the formulation of the invention to a mammal in need thereof.

In a further embodiment of the method of combating ectoparasites and/or endoparasites, the endoparasite is a helminth selected from the group consisting of *Anaplocepheda, Ancylostoma, Anecator, Ascaris, Capillaria, Cooperia, Dipyllidinum, Dirofilaria, Echinococcus, Enterobius, Fasciola, Haemonchus, Oesophagostumum, Ostertagia, Toxocara, Strongyloides, Toxascaris, Trichinella, Trichuris, Trichostrongylus* and mixtures thereof and the ectoparasites include those from the genera *Damalina, Linognathus, Solenopotes, Sarcoptes, Psoroptes, Chorioptes, Hypoderma, Lucilia, Dermatobia, Ctenocephalides, Rhipicephalus, Dermacentor, Ixodes, Ambylomma, Boophilus, Hyalomma* and mixtures thereof.

Another embodiment of the invention for combating ectoparasites and/or endoparasites in a mammal is directed to the site of injection on the mammal which is selected from the group consisting of the ear; between the shoulder near the neck; and the shoulder.

Another embodiment of the invention for combating ectoparasites and/or endoparasites in a mammal is directed to having a therapeutic effect for a period of time selected from the group consisting of at least about four months to about one year, at least about four months to about six months and at least about four months to about five months.

Another embodiment of the invention for combating ectoparasites and/or endoparasites in a mammal is directed against anthelminth selected from the group consisting of *Cooperia, Ostertagia, Haemonchus*, and mixtures thereof wherein said anthelminth is resistant to macrolide antibiotics when not administered by the method of the invention.

Further embodiments of the invention which are directed to specific elements of the invention are described below.

The bioactive agents which are used in the inventive formulations can be well known to the practitioner to which this invention pertains. Suitable bioactive agents include substances useful in preventing infection at the administration site, as for example, antiviral, antibacterial, antiparasitic, antifungal substances and combinations thereof. The agent may further be a substance capable of acting as a stimulant, sedative, hypnotic, analgesic, anticonvulsant, and the like. The delivery system can contain a large number of biologically-active agents either singly or in combination. Examples of these biologically-active agents include, but are not limited to: anti-inflammatory agents such as hydrocortisone, prednisone, fludrotisone, triamcinolone, dexamethasone, betamethasone and the like; anti-bacterial agents such as penicillins, cephalosporins, vancomycin, bacitracin, polymycins, tetracyclines, chloramphenicol, macrolides including azalides, erythromycin, streptomycin, and the like; antiparasitic agents such as quinacrine, chloroquine, quinine, and the like; antifungal agents such as nystatin, gentamicin, miconazole, tolnaftate, undecyclic acid and its salts, and the like; antiviral agents such as vidarabine, acyclovir, ribarivin, amantadine hydrochloride, iododeoxyuridine, dideoxyuridine, interferons and the like; antineoplastic agents such as methotrexate, 5-fluorouracil, bleomycin, tumor necrosis factor, tumor specific antibodies conjugated to toxins, and the like; analgesic agents such as salicylic acid, salicylate esters and salts, acetaminophen, ibuprofen, morphine, phenylbutazone, indomethacin, sulindac, tolmetin, zomepirac, and the like; local anaesthetics such as cocaine, benzocaine, novocaine, lidocaine, and the like; vaccines, or antigens, epitopes, immunogens of human or animal pathogens, such as hepatitis, influenza, measles, mumps, rubella, hemophilus, diphtheria, tetanus, rabies, polio, as well as veterinary vaccines and the like; central nervous system agents such as tranquilizers, sedatives, anti-depressants, hypnotics, B-adrenergic blocking agents, dopamine, and the like; growth factors such as colony stimulating factor, epidermal growth factor, erythropoietin, fibroblast growth factor, neural growth factor, human growth hormone, platelet derived growth factor, insulin-like growth factor, and the like; hormones such as progesterone, estrogen, testosterone, follicle stimulating hormone, chorionic gonadotrophin, insulin, endorphins, somatotropins and the like; antihistamines such as diphenhydramine, chlorpheneramine, chlorcyclizine, promethazine, cimetidine, terfenadine, and the like; cardiovascular agents such as verapamil hydrochloride, digitalis, enalapril, benazepril, streptokinase, nitroglycerine paparefine, disopyramide phosphate, isosorbide dinitrate, and the like; antiulcer agents such as cimetidine hydrochloride, sopropamide iodide, propantheline bromide, and the like; bronchodilators such as metaproternal sulfate, aminophylline, albuterol, and the like; and vasodilators such as theophylline, niacin, nicotinate esters, amylnitrate, minoxidil, diazoxide, nifedipine, and the like.

In another embodiment of the invention, the classes of bioactive agents contemplated by the inventive formulations include insecticides, acaricides, parasiticides, growth enhancers, and nonsteroidal anti-inflammatory drugs (NSAIDs). Specific classes of compounds which fall within these classes include, for example, avermectins, milbemycins, nodulisporic acid and its derivatives, estrogens, progestins, androgens, substituted pyridylmethyl derivatives, phenylpyrazoles, and COX-2 inhibitors.

The avermectin and milbemycin series of compounds are potent anthelmintic and antiparasitic agents against a wide range of internal and external parasites. The compounds which belong to this series are either natural products or are semi-synthetic derivatives thereof. The structure of these two series of compounds are closely related and they both share a complex 16-membered macrocyclic lactone ring, generically referred to by the structure below:

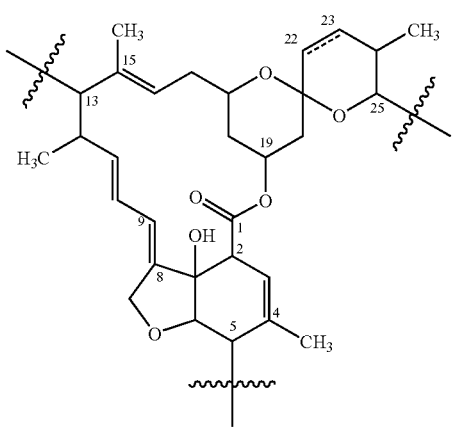

However, the milbemycins do not contain the saccharide substitutent in the 13-position of the lactone ring. The natural product avermectins are disclosed in U.S. Pat. No. 4,310,519 to Albers-Schonberg, et al., and the 22,23-dihydro avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, New York (1989). Furthermore, bioactive agents such as avermectins or ivermectin can be used in combination with other bioactive agents; and, with respect to avermectins, ivermectin, and bioactive agent combinations, reference is made to Kitano, U.S. Pat. No. 4,468,390, Beuvry et al., U.S. Pat. No. 5,824,653, von Bittera et al., U.S. Pat. No. 4,283,400, European Patent Application 0 007 812 A1, published Jun. 2, 1980, U.K. Patent Specification 1 390 336, published Apr. 9, 1975, European Patent Application 0 002 916 A2, Ancare New Zealand Patent 237 086, Bayer New Zealand Patent 176193, published Nov. 19, 1975, inter alia.

Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, N.J. (1996). Semi-synthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, and 4,920,148.

Avermectin and milbemycin-type compounds are of particular interest as they exhibit activity against a wide range endoparasites, including nematodes and roundworms, and are also effective against ectoparasites, including lice, blowflies, mites, migrating dipterous larvae, and ticks.

While many avermectin compounds are known in the art, a representative structure of the class of compounds is as follows:

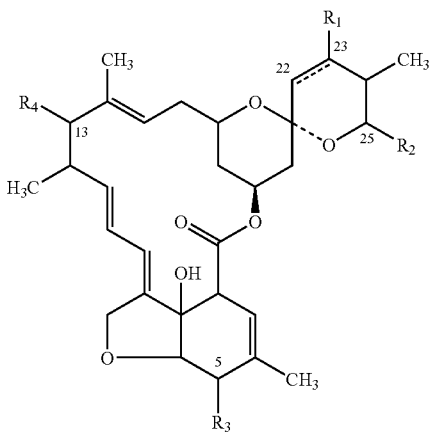

where the broken line indicates a single or a double bond at the 22,23-positions;

$R_1$ is hydrogen or hydroxy provided that $R_1$ is present only when the broken line indicates a single bond;

$R_2$ is alkyl of from 1 to 6 carbon atoms or alkenyl of from 3 to 6 carbon atoms or cycloalkyl of from 3 to 8 carbon atoms;

$R_3$ is hydroxy, methoxy or $=NOR_5$ where $R_5$ is hydrogen or lower alkyl; and $R_4$ is hydrogen, hydroxy or

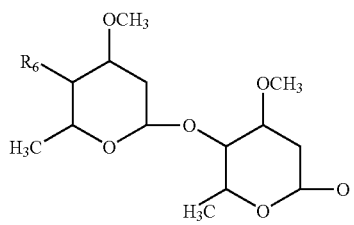

where $R_6$ is hydroxy, amino, mono-or di-lower alkylamino or lower alkanoylamino.

The preferred compounds are avermectin B1a/B1b (abamectin), 22,23-dihydro avermectin B1a/B1b (ivermectin) and the 4"-acetylamino-5-ketoximino derivative of avermectin B1a/B1b. Both abamectin and ivermectin are approved as broad spectrum antiparasitic agents.

The structures of abamectin and ivermectin are as follows:

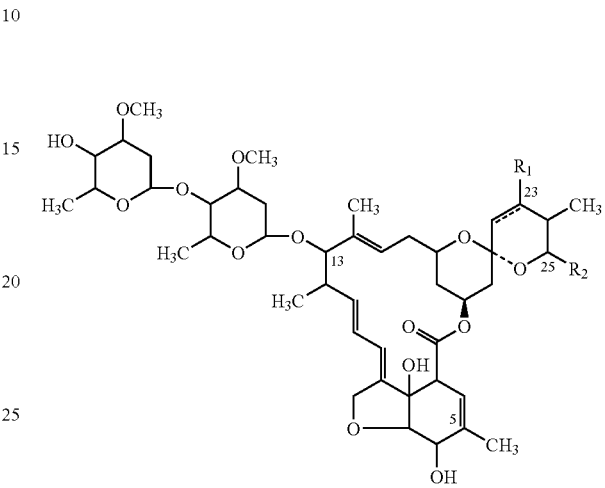

wherein for abamectin the broken line represents a double bond and $R_1$ is not present and for ivermectin the double bond represents a single bond and $R_1$ is hydrogen; and $R_2$ is isopropyl or sec-butyl.

The 4"-acetyl amino-5-ketoximino derivatives of avermectin B1a/B1b has the following structural formula:

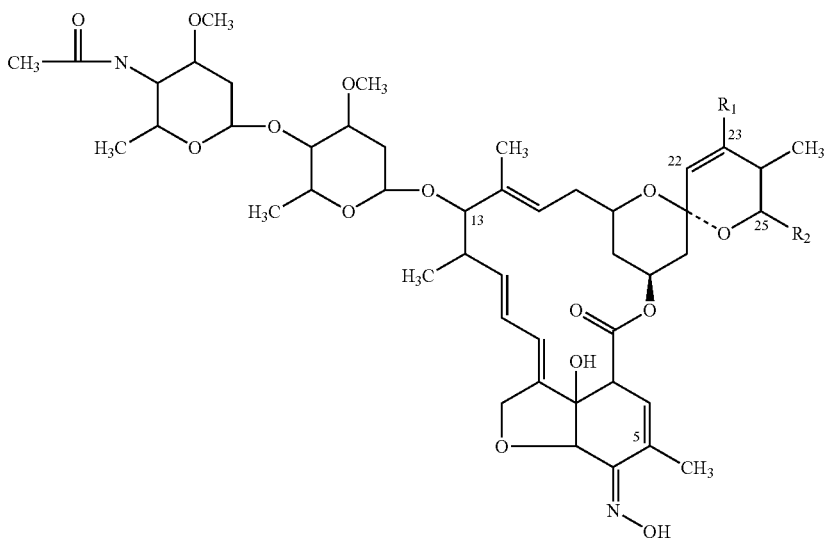

where $R_2$ is isopropyl or sec-butyl.

The avermectin products are generally prepared as a mixture of at least 80% of the compound where $R_2$ is sec-butyl and no more than 20% of the compound where $R_2$ is isopropyl.

Other preferred avermectins, include emamectin, eprinomectin, latidectin, lepimectin, selamectin and doramectin. Doramectin is disclosed in U.S. Pat. No. 5,089,490 and EP 214 738. This compound has the following structure:

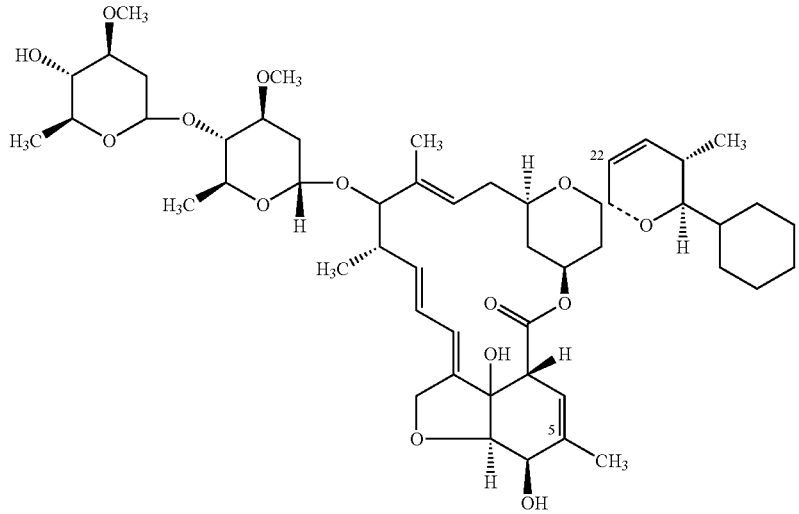

In the present formulations, ivermectin and eprinomectin are especially preferred.

A representative structure for a milbemycin is that for milbemycin $\alpha_1$:

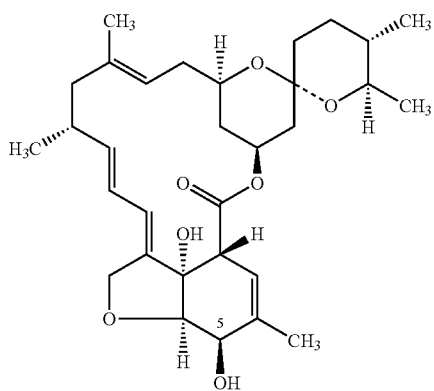

An especially preferred milbemycin is moxidectin, whose structure is as follows:

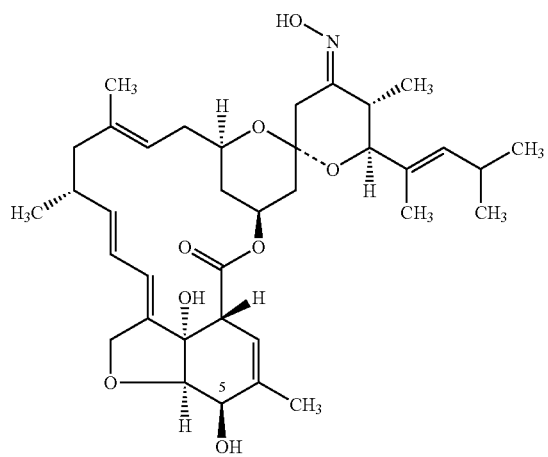 [SMILES: CC1=C[C@H]2C(=O)O[C@H]3C[C@@H](C/C=C(\C)C[C@@H](C)/C=C/C=C4\CO[C@H]([C@@H]1O)[C@@]42O)O[C@@]1(C/C(=N\O)[C@H](C)[C@@H](/C(C)=C/C(C)C)O1)C3]

The compound is disclosed in U.S. Pat. No. 5,089,490.

The monosaccharide avermectin derivatives are also preferred especially where an oxime substitution is present on the 5-position of the lactone ring. Such compounds are described, for example, in EP 667,054. Selamectin is an especially preferred compound of this class of derivatives.

In a preferred embodiment of the invention, the avermectins, milbemycins and derivatives thereof are selected from the group which includes but is not limited to, abamectin, doramectin, emamectin, eprinomectin, ivermectin, latidectin, lepimectin, and selamectin (avermectin and derivatives thereof), milbemectin, milbemycin D and moxidectin (milbemycin and derivatives thereof) and mixtures thereof.

In a particularly advantageous embodiment of the invention, the avermectins, milbemycins and derivatives thereof are selected from the group consisting of emamectin, eprinomectin, ivermectin, moxidectin and mixtures thereof.

Nodulisporic acid and its derivatives are a class of acaricidal, antiparasitic, insecticidal and anthelminitic agents known to a practitioner of the art. These compounds are used to treat or prevent infections in humans and animals. These compounds are described, for example, in U.S. Pat. No. 5,399,582 and WO 96/29073. Additionally, the compounds can be administered in combination with other insecticides, parasiticides, and acaricides. Such combinations include anthelminitic agents, such as those discussed above which include ivermectin, avermectin, eprinomectin and emamectin, as well as other agents such as thiabendazole, febantel, praziquantel, pyrantel or morantel; sulfonamide such as clorsulon, phenylpyrazoles such as fipronil; and insect growth regulators such as lufenuron. Such combinations are also contemplated in the present invention.

Generally, all classes of such insecticides may be used in this invention. One example of this class include substituted pyridylmethyl derivatives such as imidacloprid. Agents of this class are described, for example, in U.S. Pat. No. 4,742,060 or in EP 892,060.

Pyrazoles such as phenylpyrazoles and N-arylpyrazoles are another class of insecticides which possess excellent insecticidal activity against all insect pests including bloodsucking pests such as ticks, fleas etc., which are parasites on animals. This class of agents kills insects by acting on the gamma-butyric acid receptor of invertebrates. Such agents are described, for example, in U.S. Pat. No. 5,567,429, U.S. Pat. No. 5,122,530, EP 295,117, and EP 846686 A1 (or Banks GB 9625045, filed Nov. 30, 1996 also believed to be equivalent to U.S. patent Ser. No. 309,229, filed Nov. 17, 1997). In one embodiment of the invention, the N-arylpyrazoles include but are not limited to compounds of the general formula:

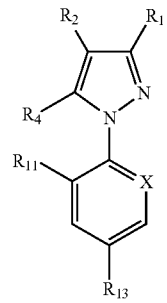

wherein:

$R_1$ is a halogen atom, CN or methyl;

$R_2$ is $S(O)_n R_3$ or 4,5-dicyanoimidazol-2-yl or haloalkyl;

$R_3$ is alkyl or haloalkyl;

$R_4$ represents a hydrogen or halogen atom or an $NR_5 R_6$, $S(O)_m R_7$, $C(O)R_7$ or $C(O)OR_7$, alkyl, haloalkyl or $OR_8$ radical or an $-N=C(R_9)(R_{10})$ radical;

$R_5$ and $R_6$ independently represent a hydrogen atom or an alkyl, haloalkyl, C(O)alkyl, $S(O)_r CF_3$ or alkoxycarbonyl radical or $R_5$ and $R_6$ can together form a divalent alkylene radical which is optionally interrupted by one or two divalent heteroatoms;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents an optionally substituted aryl or an optionally substituted heteroaryl group;

$R_{11}$ and $R_{12}$ represent, independently of one another, hydrogen, halogen CN or $NO_2$;

$R_{13}$ represents a halogen atom or a haloalkyl, haloalkoxy, $S(O)_q CF_3$ or $SF_5$ group;

m, n, q and r represent, independently of one another, an integer equal to 0, 1 or 2;

X represents a trivalent nitrogen atom or a $C-R_{12}$ radical, the three other valencies of the carbon atom forming part of the aromatic ring;

with the proviso that, when $R_1$ is methyl, then either $R_3$ is haloalkyl, $R_4$ is $NH_2$, $R_{11}$ is Cl, $R_{13}$ is $CF_3$ and X is N or else $R_2$ is 4,5-dicyanoimidazol-2-yl, $R_4$ is Cl, $R_{11}$ is Cl, $R_{13}$ is $CF_3$ and X is C—Cl;

In one embodiment of this particular invention, reference to alkyl, haloalkyl, halalkoxy describe moieties with 1 to 8 carbon atoms. In another embodiment of this particular invention, reference to alkyl, haloalkyl, halalkoxy describe moieties with 1 to 4 carbon atoms.

Fipronil is well known in the art as a flea and tick agent. It would be well within the skill level of the practitioner to decide which individual compounds can be used in the inventive formulations. Other preferred phenyl pyrazoles include the following compounds:

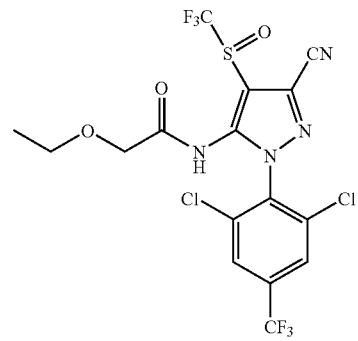

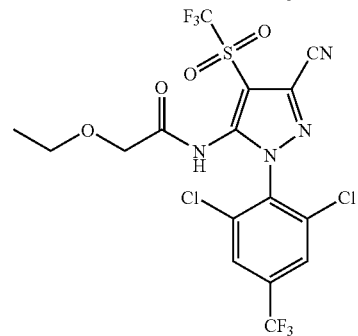

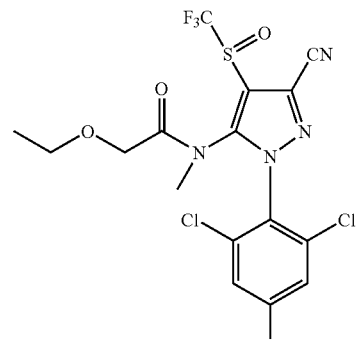

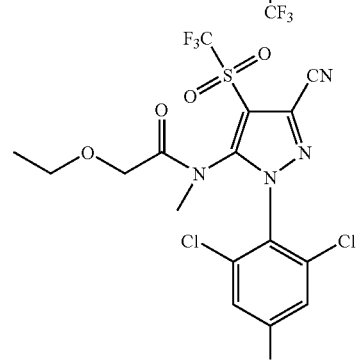

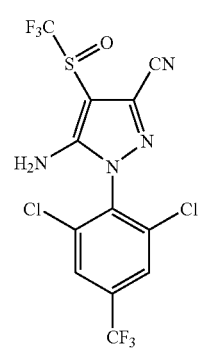

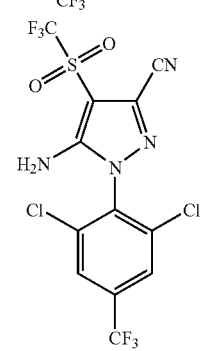

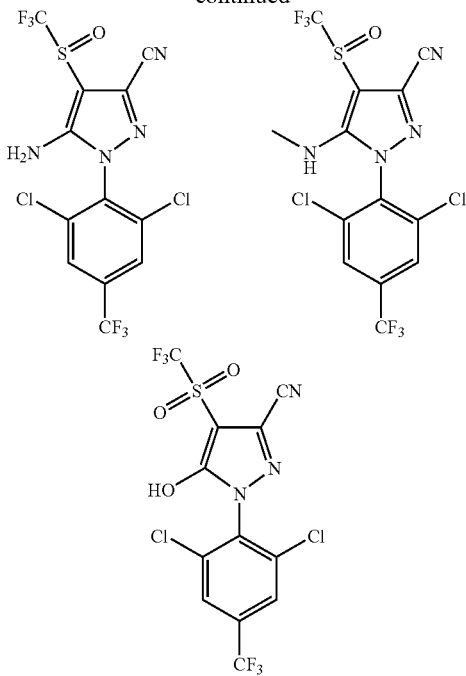

Especially preferred phenylpyrazoles in addition to fipronil include fipronil thio

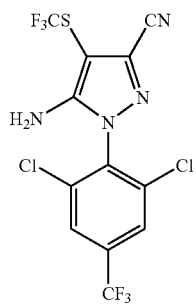

and fipronil sulfone

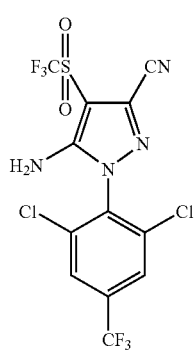

Insect growth regulators (IGRs) are another class of insecticides or acaricides, which are also provided for in the inventive formulations. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356; 3,818,047; 4,225,598; 4,798,837; and 4,751,225, as well as in EP 179,022 or U.K. 2,140,010. Especially advantageous insect growth regulators include diflubenzuron, lufenuron, methoprene, phenoxycarb, pyriproxyfen, and cyromazine. Again, it would be well within the skill level of the practitioner to decide which individual compounds can be used in the inventive formulation.

Estrogens, progestins, and androgens refers to classes of chemical compounds which are also well known to a practitioner in this art. In fact, estrogens and progestins are among the most widely prescribed drugs and are used, for example, alone or in combination for contraception or hormone replacement therapy in post menopausal women. Estrogens and progestins occur naturally or are prepared synthetically. This class of compounds also includes estrogens or progesterone receptor antagonists. Antiestrogens, such as tamoxifen and clomiphene, are used to treat breast cancer and infertility. Antiprogestives are used as contraceptives and anticancer drugs, as well as to induce labor or terminate a pregnancy.

The androgens and antiandrogens structurally related to the estrogens and progestins as they are also biosynthesized from cholesterol. These compounds are based on testosterone. Androgens are used for hypogonadism and promote muscle development. Antiandrogens are used, for example, in the management of hyperplasia and carcinoma of the prostate, acne, and male pattern baldness as well as in the inhibition of the sex drive in men who are sex offenders. Estrogen, progestins, and androgens are described, for example, in "Goodman & Gilman's The Pharmacological Basis of Therapeutics," $10^{th}$ ed., J. G. Hardman and L. E. Limbird, eds., Chapters 58 and 59, pp. 1597-1648, McGraw Hill, New York (2001) or in "Principles of Medicinal Chemistry," $3^{rd}$ ed., W. O. Foye, ed., Chapter 21, pp. 433-480, Lea & Febiger, Philadelphia (1989).

Estrogens, progestins and androgens are also used in animal husbandry as growth promoters for food animals. It is known in the art that compounds of these classes act as growth-promoting steroids in animals such as cattle, sheep, pigs, fowl, rabbits, etc. Delivery systems to promote the growth of animals are described, for example, in U.S. Pat. Nos. 5,401,507; 5,288,469; 4,758,435; 4,686,092; 5,072,716 and 5,419,910.

NSAIDs are well known in the art. The classes of compounds which belong to this group include salicylic acid derivatives, para-aminophenol derivatives, indole and indene acetic acids, heteroaryl acetic acids, arylpropionic acids, anthranilic acids (fenamates), enolic acids, and alkanones. NSAIDs exert their activity by interfering with prostaglandin biosynthesis by irreversibly or reversibly inhibiting cycloxygenase. Also included are COX-2 inhibitors which act by inhibiting the COX-2 receptor. Compounds of this group possess analgesic, antipyretic and nonsteroidal anti-inflammatory properties. Compounds belonging to these classes are described, for example, in Chapter 27 of Goodman and Gilman on pages 687 to 731 or in Ch. 23 of Foye on pages 503 to 530 as well as in U.S. Pat. Nos. 3,896,145; 3,337,570; 3,904,682; 4,009,197; 4,223,299; and 2,562,830, as well as the specific agents listed in The Merck Index. Examples of COX-2 inhibitors include firocoxib, deracoxib, rofecoxib, celecoxib, carprofen, meloxicam and nimesulide.

Macrolides are a class of antibiotics which contain a many-membered lactone ring to which are attached one or more deoxy sugars. Macrolides are generally bacteriostatic, but have been shown to be bacteriocidal in high concentration against very susceptible organisms. Macrolides are most effective against gram-position cocci and bacilli, although they do possess some activity against some gram-negative organism. Macrolides exert their bacteriostatic activity by inhibiting bacterial protein synthesis by binding reversibly to the 50 S ribosomal subunit. ("Goodman & Gilman's the Pharmacological Basis of Therapeutics," 9th ed., J. G. Hardman & L. E. Limbird, eds., ch. 47, pp. 1135-1140, McGraw-Hill, New York (1996)).

The macrolides as a class are colorless and usually crystalline. The compounds are generally stable in near neutral solution, but they only have limited stability in acid or base solutions. The reason for this is because the glycosidic bonds hydrolyze in acid and the lactone ring saponifies in base ("Principles of Medicinal Chemistry," 2nd ed., W. F. Foye, ed., ch. 31, pp. 782-785, Lea & Febiger, Philadelphia (1981)). Hence, there is a need for pharmaceutical or veterinary compositions for parenteral, e.g., intravenous, intramuscular, subcutaneous, administration of macrolide antibiotics.

The bioactive agent in the present invention can be a macrolide, as macrolides are soluble in many organic solvents but are only slightly water soluble. Solutions of macrolides in organic solvent systems are used in human and veterinary practice for administration by the intramuscular and subcutaneous routes.

Macrolides as a class include the erythromycin and its derivatives as well as other derivatives such as the azalides. Erythromycin (MW 733.94 daltons) is the common name for a macrolide antibiotic produced by the growth of a strain of Streptomyces erythreous. It is a mixture of three erythromycins, A, B and C consisting largely of erythromycin A. Its chemical name is (3R*, 4S*, 5S*, 6R*, 7R*, 9R*, 11R*, 12R*, 13S*, 14R*)-4-[(2,6-dideoxy-3-C-methyl-3-O-methyl-.alpha.-L-ribo-hexopyranosyl)-oxy]-14-ethyl-7,12,13-trihydroxy-3,5,7,9,11,13-hexamethyl-6[[3,4,6-trideoxy-3-(dimethylamino)-.beta.-D-xylo-hexapyranosyl]oxy] oxacyclotetradecane-2,10-dione, $(C_{37}H_{67}NO_{13})$.

Erythromycin has a broad and essentially bacteriostatic action against many Gram-positive and some Gram-negative bacteria as well as other organisms including mycoplasmas, spirochetes, chlamydiae and rickettsiae. In humans, it finds usefulness in the treatment of a wide variety of infections. It finds wide application in veterinary practice in the treatment of infectious diseases such as pneumonias, mastitis, metritis, rhinitis, and bronchitis in cattle, swine and sheep.

Other derivatives of erythromycins include carbomycin, clarithromycin, josamycin, leucomycins, midecamycins, mikamycin, miokamycin, oleandomycin, pristinamycin, rokitamycin, rosaramicin, roxithromycin, spiramycin, tylosin, troleandomycin, and virginiamycin. As with the erythromycins, many of these derivatives exist as component mixtures. For example, carbomycin is a mixture of carbomycin A and carbomycin B. Leucomycin exists as a mixture of components $A_1$, $A_2$, $A_3$, $A_9$, $B_1$—$B_4$, U and V in various proportions. Component $A_3$ is also known as josamycin and leucomycin V is also known as miokomycin. The major components of the midecamycins is midecamycin A and the minor components are midecamycins $A_2$ $A_3$ and $A_4$. Likewise, mikamycin is a mixture of several components, mikamycin A and B. Mikamycin A is also known as virginiamycin $M_1$ Pristinamycin is composed of pristinamycins $I_A$, $I_B$, and $I_C$, which are identical to virginiamycins $B_2$, $B_{13}$ and $B_2$ respectively, and pristinamycin $II_A$ and $II_B$, which are identical to virginiamycin $M_1$ and 26,27-dihydrovirginiamycin $M_1$. Spiramycin consists of three components, spiromycin I, II, and III. Virginiamycin is composed of virginiamycin $S_1$, and virginiamycin $M_1$. All these components may be used in this invention. Sources of these macrolides are well known to the practitioner and are described in the literature in references such as "The Merck Index," 12th ed., S. Budarari, ed., Merck & Co., Inc., Whitehouse Station, N.J. (1996).

The azalides are semisynthetic macrolide antibiotics related to erythromycin A and exhibit similar solubility characteristics. Azalides are semisynthetic macrolides antibiotics related to erythromycin A and exhibit similar solubility characteristics. This class includes compounds of the general structure:

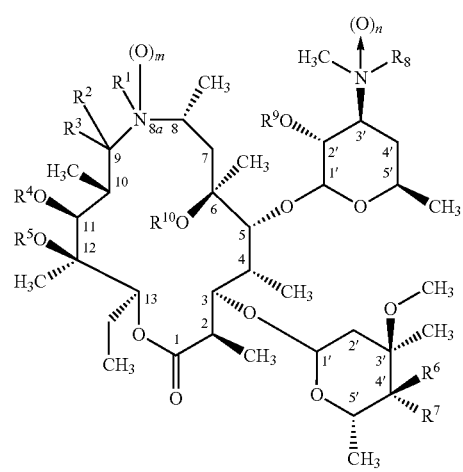

and the pharmaceutically acceptable salts and esters thereof, and the pharmaceutically acceptable metal complexes thereof, wherein $R^1$ is hydrogen; hydroxy; $C_{1-4}$ alkoxy; formyl; $C_{1-10}$ alkylcarbonyl, $C_{1-10}$ alkoxycarbonyl, aryloxycarbonyl, $C_{1-10}$ aralkoxycarbonyl, $C_{1-10}$ alkylsulfonyl, or arylsulfonyl wherein said $C_{1-10}$ alkyl group or aryl group is unsubstituted or substituted by 1-3 halo (F, Cl, Br), hydroxy, amino, $C_{1-5}$ acylamino or $C_{1-4}$ alkyl groups; or unsubstituted or substituted $C_{1-10}$ alkyl, $C_{2-10}$ alkenyl or $C_{2-10}$ alkynyl wherein said substituents are independently 1-3 of (a) aryl or heteroaryl optionally substituted by 1-3 halo (F, Cl, Br, I), $C_{1-4}$ alkyl, $C_{1-3}$ alkoxy, amino, $C_{1-4}$ alkylamino, di($C_{1-4}$ alkyl)amino or hydroxy, (b) heterocyclyl optionally substituted by hydroxy, amino, $C_{1-4}$ alkylamino, di($C_{1-4}$ alkyl)amino, $C_{1-4}$ alkylcarbonyloxy or $C_{1-4}$ alkylcarbonylamino, (c) halo (F, Cl, Br or I), (d) hydroxy optionally acylated by a group

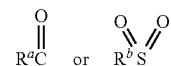

wherein $R^a$ is hydrogen, $C_{1-6}$ alkyl, aryl, heteroaryl, aralkyl, or heteroaralkyl and $R^b$ is $C_{1-6}$ alkyl or aryl, (e) $C_{1-10}$ alkoxy, (f) aryloxy or heterocaryloxy optionally substituted by 1-3 halo, hydroxy, amino or $C_{1-4}$ alkyl groups, (g) amino or $C_{1-10}$ alkylamino optionally acylated by a group

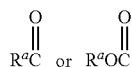

or $R^bSO_2$, wherein $R^a$ and $R^b$ are as defined above, (h) di($C_{1-10}$ alkyl)amino, (i) arylamino, heteroarylamino, aralkylamino or heteroarylakylaamino wherein said aryl or heteroaryl group is optionally substituted by 1-3 halo, hydroxy, amino or $C_{1-4}$ alkyl groups, (j) mercapto, (k) $C_{1-10}$ alkylthio, alkylsulfinyl or alkylsulfonyl, arylthio, arylsulfinyl or arylsulfonyl wherein said aryl group is optionally substituted by 1-3 halo, hydroxy, amino or $C_{1-4}$ alkyl groups, (l) formyl, (m) $C_{1-10}$ alkylcarbonyl, (n) arylcarbonyl, heteroarylcarbonyl, aralkylcarbonyl or heteroarylalkylcarbonyl wherein said aryl or heteroaryl group is optionally substituted by 1-3 halo, hydroxy, amino or $C_{1-4}$ alkyl groups, (o) carboxy, (p) $C_{1-10}$ alkoxycarbonyl, (q) aryloxycarbonyl, heteroaryloxycarbonyl, aralkoxycarbonyl or heteroarylalkoxycarbonyl wherein said aryl or heteroaryl group is optionally substituted by 1-3 halo, hydroxy, amino or $C_{1-4}$ alkyl groups, (r) carbamoyl or sulfamoyl wherein the N-atom is optionally substituted by 1-2 $C_{1-6}$ alkyl groups or by a $C_{4-6}$ alkylene chain, (s) cyano, (t) isonitrilo, (u) nitro, (v) azido, (w) iminomethyl optionally substituted on nitrogen or carbon with $C_{1-10}$ alkyl, (y) oxo, or (x) thiono;

wherein said alkyl chain, if more than two carbons in length, can be optionally interrupted by 1-2 oxa, thia or aza (—NR-wherein R is hydrogen or $C_{1-3}$ alkyl) groups.

$R^{10}$ is hydrogen or $R^1$ and $R^{10}$ together are $C_1$-$C_3$ alkylene optionally substituted by an oxo group;

$R^1$ and $R^4$ together are $C_1$-$C_3$ alkylene optionally substituted by an oxo group $R^2$ and $R^3$ are hydrogen, $C_{1-10}$ alkyl, aryl $R^2$ and $R^3$ together are oxo and thiono;

$R^4$ and $R^5$ are independently hydrogen and alkylcarbonyl;

$R^4$ and $R^5$ are together carbonyl;

$R^6$ and $R^7$ are both hydrogen or one of $R^6$ and $R^7$ is hydrogen and the other is hydroxy, an acyloxy derivative taken from the group consisting of formyloxy, $C_{1-10}$ alkylcarbonyloxy, arylcarbonyloxy and aralkylcarbonyloxy, or —$NHR^{12}$ wherein $R^{12}$ is hydrogen, arylsulfonyl or heteroarylsulfonyl optionally substituted by 1-3 halo or $C_{1-3}$ alkyl groups, alkylsulfonyl, or

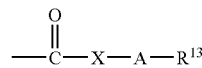

where

X is a connecting bond, O or NH,

A is a connecting bond or $C_1$-$C_3$ alkylene $R^{13}$ is hydrogen, $C_1$-$C_{10}$ alkyl, aryl, aralkyl, heteroaryl, heterocyclyl, or $C_3$-$C_7$ cycloalkyl, any of which $R^{13}$ groups other than hydrogen can be substituted by one or more of halogen, hydroxyl, $C_1$-$C_3$ alkoxy, cyano, isonitrilo, nitro, amino, mono- or di-($C_1$-$C_3$)alkylamino, mercapto, $C_1$-$C_3$ alkylthio, $C_1$-$C_3$ alkylsulfinyl, $C_1$-$C_3$ alkylsulfonyl, arylthio, arylsulfinyl, sulfamoyl, arylsulfonyl, carboxy, carbamoyl, $C_1$-$C_3$ alkylcarbonyl, or $C_1$-$C_3$ alkoxycarbonyl;

$R^6$ and $R^7$ are together oxo, hydroxyimino, alkoxyimino, aralkoxyimino or aminoimino;

$R^8$ is methyl, aralkoxycarbonyl, and arylsulfonyl;

$R^9$ is hydrogen, formyl, $C_{1-10}$ alkylcarbonyl, $C_{1-10}$ alkoxycarbonyl, and arylalkoxycarbonyl;

m and n are independently integers of zero or one; and said metal complex is taken from the group consisting of copper, zinc, cobalt, nickel and cadmium.

These compounds are disclosed in EP 568 699, herein incorporated by reference. Azalides as a class of components is well-known in the art and further derivatives are described, for example, in U.S. Pat. Nos. 5,869,629; 5,629,296; 5,434,140; 5,332,807; 5,250,518; 5,215,890; and 5,210,235, all incorporated herein by reference.

Particularly preferred is azithromycin. The structure of azithromycin is

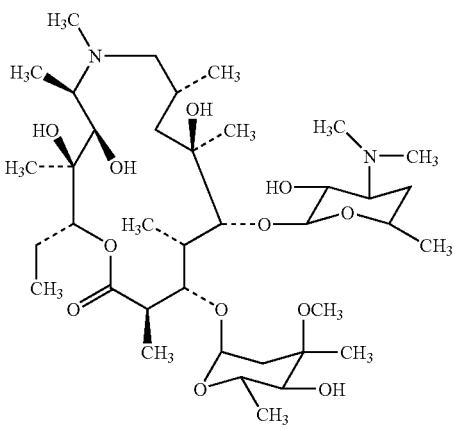

Compounds termed herein formula I and formula II have the following structures:

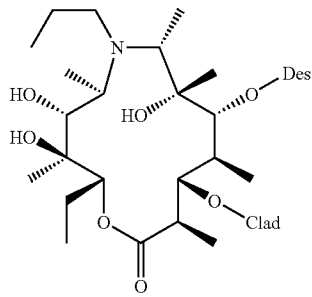

wherein Des is desosomine and Clad is cladinose (formula I) and

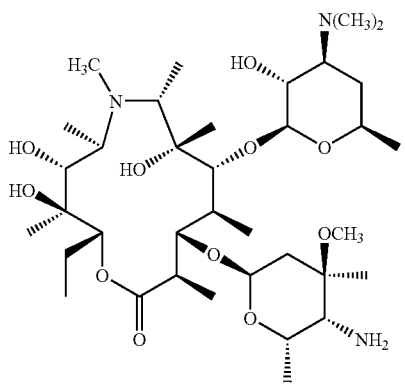

(formula II). The compound of formula II are also known as 8a-azalide. These compounds are disclosed in EP 508 699, herein incorporated by reference. The corresponding basic and acid addition salts and ester derivatives of the macrolides, including the azalides compounds, are also contemplated. These salts are formed from the corresponding organic or inorganic acids or bases. These derivatives include the customary hydrochloride and phosphate salts as well as the acetate, propionate and butyrate esters. These derivatives may have different names. For example, the phosphate salt of oleandomycin is matromycin and the triacetyl derivative is troleandomycin. Rokitamycin is leucomycin V 4-B-butanoate, 3B-propionate.

This invention includes all nodulisporic acid derivatives know in the art, including all steroisomers, such as those described in the prior publication described above, which are expressly incorporated by reference. Especially preferred are spot-on formulations comprising nordulisporic acid derivatives of the formula:

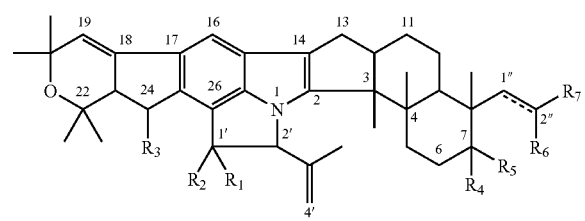

wherein
$R_1$ is (1) hydrogen,
 (2) optionally substituted alkyl,
 (3) optionally substituted alkenyl,
 (4) optionally substituted alkynyl,
 (5) optionally substituted cycloalkyl,
 (6) optionally substituted cycloalkenyl,
 where the substituents on the alkyl, alkenyl, alkynyl, cycloalkyl and cycloalkenyl are 1 to 3 groups independently selected from
  (i) alkyl,
  (ii) alkyl, where X is O or $S(O)_m$.
  (iii) cycloalkyl,
  (iv) hydroxy,
  (v) halogen,
  (vi) cyano,
  (vii) carboxy,
  (viii) $NY^1Y^2$, where $Y^1$ and $Y^2$ are independently H or alkyl,
  (ix) alkanoylamino, and
  (x) aroylamino wherein said aroyl is optionally substituted with 1 to 3 groups independently selected from $R^f$
 (7) aryl or arylalkyl, wherein said aryl is optionally substituted with 1 to 3 groups independently selected from $R^f$,
 (8) perfluoroalkyl
 (9) a 5- or 6-member heterocycle containing from 1 to 4 heteroatoms independently selected from oxygen, sulfur and nitrogen atoms optionally substituted by 1 to 3 groups independently selected from hydroxy, oxo, alkyl and halogen, and which may be saturated or partly unsaturated,
$R_2$, $R_3$, and $R_4$ are independently $OR^a$, $OCO_2R^b$, $OC(O)NR^cR^d$; or
$R_1$ and $R_2$ represent =O, =$NOR^a$ or =N—$NR^cR^d$;
$R_5$ and $R_6$ are H; or
$R_5$ and $R_6$ together represent —O—;
$R_7$ is (1) CHO, or
 (2) the fragment

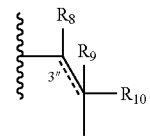

$R_8$ is (1) H,
 (2) $OR^a$, or
 (3) $NR^cR^d$
$R_9$ is (1) H, or
 (2) $OR^a$;
$R_{10}$ is (1) CN,
 (2) $C(O)OR^b$,
 (3) $C(O)N(OR^b)R^c$,
 (4) $C(O)NR^cR^d$,
 (5) $NHC(O)OR^b$,
 (6) $NHC(O)NRCR^d$,
 (7) $CH_2OR^a$,
 (8) $CH_2OCO_2R^b$,
 (9) $CH_2OC(O)NR^cR^d$,
 (10) $C(O)NR^cNR^cR^d$, or
 (11) $C(O)NR^cSO_2R^b$;
----- represents a single or a double bond;
$R^a$ is (1) hydrogen,
 (2) optionally substituted alkyl,
 (3) optionally substituted alkenyl,
 (4) optionally substituted alkynyl, (5) optionally substituted alkanoyl,
(6) optionally substituted alkenoyl,
(7) optionally substituted alkynoyl,
(8) optionally substituted aroyl,
(9) optionally substituted aryl,
(10) optionally substituted cycloalkanoyl,
(11) optionally substituted cycloalkenoyl,
(12) optionally substituted alkylsulfonyl
(13) optionally substituted cycloalkyl
(14) optionally substituted cycloalkenyl
where the substituents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 10 groups independently selected from hydroxy, alkoxy, cycloalkyl, arylalkoxy, $NR^gR^h$, $CO_2R_b$, $CONR^cR^d$ and halogen,
(15) perfluoroalkyl,
(16) arylsulfonyl optionally substituted with 1 to 3 groups independently selected from alkyl, perfluoroalkyl, nitro, halogen and cyano,
(17) a 5- or 6-member heterocycle containing 1 to 4 heteroatoms selected from oxygen, sulfur and nitrogen optionally substituted by 1 to 4 groups independently selected from alkyl, alkenyl, perfluoroalkyl, amino, $C(O)NR^cR^d$, cyano, $CO_2R^b$ and halogen, and which may be saturated or partly unsaturated;

$R^b$ is (1) H,
(2) optionally substituted aryl,
(3) optionally substituted alkyl,
(4) optionally substituted alkenyl,
(5) optionally substituted alkynyl,
(6) optionally substituted cycloalkyl,
(7) optionally substituted cycloalkenyl, or
(8) optionally substituted
heterocycle containing from 1 to 4 heteroatoms independently selected from oxygen, sulfur and nitrogen; where the substituents on the aryl, alkyl, alkenyl, cycloalkyl, cycloalkenyl, heterocycle, or alkynyl are from 1 to 10 groups independently selected from
(i) hydroxy,
(ii) alkyl,
(iii) oxo,
(iv) $SO_2NR^gR^h$,
(v) arylalkoxy,
(vi) hydroxyalkyl,
(vii) alkoxy,
(viii) hydroxyalkoxy,
(ix) aminoalkoxy,
(x) cyano,
(xi) mercapto,
(xii) alkyl-$S(O)_m$,
(xiii) cycloalkyl optionally substituted
with 1 to 4 groups independently selected from $R^e$,
(xiv) cycloalkenyl,
(xv) halogen,
(xvi) alkanoyloxy,
(xvii) $C(O)NR^gR^h$,
(xviii) $CO_2R^i$,
(xix) formyl,
(xx) —$NR^gR^h$,
(xxi) 5 to 9-member heterocycle, which may be saturated or partially unsaturated, containing from 1 to 4 heteroatoms independently selected from oxygen, sulfur and nitrogen, and optionally substituted with 1 to 5 groups independently selected from $R^e$,
(xxii) optionally substituted aryl, wherein the aryl substituents are 1,2-methylenedioxy or 1 to 5 groups independently selected from $R^e$,
(xxiii) optionally substituted arylalkoxy, wherein the aryl substituents are 1,2-methylenedioxy or 1 to 5 groups independently selected from $R^e$, and
(xxiv) perfluoroalkyl;

$R^c$ and $R^d$ are independently selected from $R^b$; or
$R^c$ and $R^d$ together with the N to which they are attached form a 3- to 10-member ring containing 0 to 2 additional heteroatoms selected from O, $S(O)_m$, and N, optionally substituted with 1 to 3 groups independently selected from $R^g$, hydroxy, thioxo and oxo;

$R^e$ is (1) halogen,
(2) alkyl,
(3) perfluoroalkyl,
(4) —$S(O)_mR^i$,
(5) cyano,
(6) nitro,
(7) $R_{10}(CH_2)v$-,
(8) $R^iCO_2(CH_2)v$-,
(9) $R^iOCO(CH_2)v$-,
(10) optionally substituted aryl where the substituents are from 1 to 3 of halogen, alkyl, alkoxy, or hydroxy,
(11) $SO_2NR^gR^h$, or
(12) amino;

$R^f$ is (1) alkyl,
(2) X—$C_1$-$C_4$ alkyl, where X is O or $S(O)_m$,
(3) alkenyl,
(4) alkynyl,
(5) perfluoroalkyl,
(6) $NY^1Y^2$, where $Y^1$ and $Y^2$ are independently H or alkyl,
(7) hydroxy,
(8) halogen, and
(9) alkanoylamino, $R^g$ and $R^h$ are independently
(1) hydrogen,
(2) alkyl optionally substituted with hydroxy, amino, or $CO_2R^i$
(3) aryl optionally substituted with halogen, 1,2-methylenedioxy, alkoxy, alkyl or perfluoroalkyl,
(4) arylalkyl, wherein the aryl is optionally substituted with perfluorolkyl or 1,2-methylenedioxy;
(5) alkoxycarbonyl,
(6) alkanoyl,
(7) alkanoylalkyl,
(9) aryl alkoxycarbonyl,
(10) aminocarbonyl,
(11) monoalkylaminocarbonyl
(12) dialkylaminocarbonyl; or
$R^g$ and $R^h$ together with the N to which they are attached form a 3- to 7-member ring containing 0 to 2 additional heteroatoms selected from O, $S(O)_m$, and N, optionally substituted with 1 to 3 groups independently selected from $R^e$ and oxo;

$R^i$ is (1) hydrogen,
(2) perfluoroalkyl,
(3) alkyl,
(4) optionally substituted aryl or arylalkyl, where the aryl substituents are from 1 to 3 groups independently selected from halogen, alkyl, alkoxy, and hydroxy;

m is 0 to 2; and
v is 0 to 3; or
a pharmaceutically acceptable salt thereof.

In a preferred embodiment, the present invention provides compounds of Formula I wherein $R_1$ is (1) hydrogen,
- (2) optionally substituted alkyl,
- (3) optionally substituted alkenyl,
- (4) optionally substituted alkynyl,
- (5) optionally substituted cycloalkyl,
- (6) optionally substituted cycloalkenyl where the substituents on the alkyl, alkenyl, alkynyl, cycloalkyl and cycloalkenyl are 1 to 3 groups independently selected from
  - (i) alkyl,
  - (ii) X—$C_1$-$C_6$ alkyl, where X is O or $S(O)_m$,
  - (iii) cycloalkyl,
  - (iv) hydroxy,
  - (v) halogen,
  - (vi) cyano,
  - (vii) carboxy, and
  - (viii) $NY^1Y^2$, where $Y^1$ and $Y^2$ are independently H or alkyl,
- (7) aryl or arylalkyl wherein said aryl is optionally substituted with 1 to 3 groups independently selected from $R^f$,
- (8) perfluoroalkyl,
- (9) a 5- or 6-member heterocycle containing from 1 to 4 heteroatoms independently selected from oxygen, sulfur and nitrogen atoms optionally substituted by 1 to 3 groups independently selected from hydroxy, oxo, alkyl and halogen, and which may be saturated or partly unsaturated, $R_8$ is (1) H,
- (2) OH, or
- (3) $NH_2$;

$R_9$ is (1) H or
- (2) OH;

$R_{10}$ is (1) $C(O)OR^b$,
- (2) $C(O)N(OR^b)R^c$,
- (3) $C(O)NR^cR^d$,
- (4) $NHC(O)OR^b$,
- (5) $NHC(O)NR^cR^d$,
- (6) $CH_2OR^a$,
- (7) $CH_2OCO_2R^b$,
- (8) $CH_2OC(O)NR^cR^d$,
- (9) $C(O)NR^cNR^cR^d$, or
- (10) $C(O)NR^cSO_2R^b$;

$R^a$ is (1) hydrogen,
- (2) optionally alkyl,
- (3) optionally substituted alkenyl,
- (4) optionally substituted alkynyl,
- (5) optionally substituted alkanoyl,
- (6) optionally substituted alkenoyl,
- (7) optionally substituted alkynoyl,
- (8) optionally substituted aroyl,
- (9) optionally substituted aryl,
- (10) optionally substituted cycloalkanoyl,
- (11) optionally substituted cycloalkenoyl,
- (12) optionally substituted alkylsulfonyl
- (13) optionally substituted cycloalkyl
- (14) optionally substituted cycloalkenyl where the substituents on the alkyl, alkenyl, alkynyl, alkanoyl, alkenoyl, alkynoyl, aroyl, aryl, cycloalkanoyl, cycloalkenoyl, alkylsulfonyl, cycloalkyl and cycloalkenyl are from 1 to 10 groups independently selected from hydroxy, alkoxy, cycloalkyl, aryl alkoxy, $NR^gR^h$, $CO_2R^b$, $CONR^cR^d$ and halogen,
- (15) perfluoroalkyl,
- (16) arylsulfonyl optionally substituted with 1 to 3 groups independently selected from alkyl, perfluoroalkyl, halogen and cyano,
- (17) a 5- or 6-member heterocycle containing 1 to 4 heteroatoms selected from oxygen, sulfur and nitrogen optionally substituted by 1 to 4 groups independently selected from alkyl, alkenyl, perfluoroalkyl, amino, $C(O)NR^cR^d$, cyano, $CO_2R^b$ and halogen, and which may be saturated or partly unsaturated;

$R^b$ is (1) H,
- (2) optionally substituted aryl,
- (3) optionally substituted alkyl,
- (4) optionally substituted alkenyl,
- (5) optionally substituted alkynyl,
- (6) optionally substituted cycloalkyl,
- (7) optionally substituted cycloalkenyl, or
- (8) optionally substituted 5- to 10-member heterocycle containing from 1 to 4 heteroatoms independently selected from oxygen, sulfur and nitrogen; where the substituents on the aryl, alkyl, alkenyl, cycloalkyl, cycloalkenyl, heterocycle, or alkynyl are from 1 to 10 groups independently selected from
- (i) hydroxy,
- (ii) $C_1$-$C_3$ alkyl,
- (iii) oxo,
- (iv) $SO_2NR^gR^h$,
- (v) aryl alkoxy,
- (vi) hydroxy alkyl,
- (vii) alkoxy,
- (viii) hydroxyalkoxy,
- (ix) aminoalkoxy,
- (x) cyano,
- (xi) perfluoroalkyl,
- (xii) alkyl-$S(O)_m$,
- (xiii) cycloalkyl optionally substituted
with 1 to 4 groups independently selected from $R^e$,
- (xiv) cycloalkenyl,
- (xv) halogen,
- (xvi) alkanoyloxy,
- (xvii) $C(O)NR^gR^h$,
- (xviii) $CO_2R^i$,
- (xix) optionally substituted arylalkoxy,
wherein the aryl substituents are 1,2-methylenedioxy or 1 to 5 groups independently selected from $R^e$,
- (xx) —$NR^gR^h$,
- (xxi) 5 to 6-member heterocycle, which may be saturated or partially unsaturated, containing from 1 to 4 heteroatoms independently selected from oxygen, sulfur and nitrogen, and optionally substituted with 1 to 5 groups independently selected from $R^e$, and
- (xxii) optionally substituted aryl, wherein the aryl substituents are 1,2-methylenedioxy or 1 to 5 groups independently selected from $R^e$;

$R^e$ is (1) halogen,
- (2) alkyl,
- (3) perfluoroalkyl,
- (4) —$S(O)_mR^i$,
- (5) cyano,
- (6) amino,
- (7) $R^iO(CH_2)_v$—,
- (8) $R^iCO_2(CH_2)_v$—,
- (9) $R^iOCO(CH_2)_v$—,
- (10) optionally substituted aryl where the substituents are from 1 to 3 of halogen, alkyl, alkoxy, or hydroxy, or
- (11) $SO_2NR^gR^h$;

$R^f$ is (1) methyl,
(2) X—C1-C2 alkyl, where X is O or $S(O)_m$,
(3) halogen,
(4) acetylamino,
(5) trifluoromethyl,
(6) $NY^1Y^2$, where $Y^1$ and $Y^2$ are independently H or methyl, and
(7) hydroxy;

$R^g$ and $R^h$ are independently
(1) hydrogen,
(2) alkyl optionally substituted with hydroxy, amino, or $CO_2R^i$
(3) aryl optionally substituted with halogen, 1,2-methylenedioxy, alkoxy, alkyl or perfluoroalkyl,
(4) arylalkyl, wherein the aryl is optionally substituted with perfluorolkyl or 1,2-methylenedioxy;
(5) alkoxycarbonyl,
(6) alkanoyl,
(7) alkanoyl alkyl,
(9) arylalkoxycarbonyl,
(10) aminocarbonyl,
(11) monoalkylaminocarbonyl
(12) dialkylaminocarbonyl; or $R^g$ and $R^h$ together with the N to which they are attached form a 5- to 6-member ring containing 0 to 2 additional heteroatoms selected from O, $S(O)_m$, and N, optionally substituted with 1 to 3 groups independently selected from $R^e$ and oxo;

$R^i$ is (1) hydrogen,
(2) perfluoroalkyl,
(3) alkyl,
(4) optionally substituted arylalkyl, where the aryl substituents are from 1 to 3 groups independently selected from halogen, alkyl, alkoxy, and hydroxy; all other variables are as defined under Formula I.

In another preferred embodiment, the present invention provides compounds of Formula I wherein $R^i$ is (1) hydrogen,
(2) optionally substituted alkyl,
(3) optionally substituted alkenyl,
(4) optionally substituted alkynyl,
where the substituents on the alkyl, alkenyl, and alkynyl are 1 to 3 groups independently selected from
(i) methyl,
(ii) X-methyl, where X is O or $S(O)_m$ and
(iii) halogen,
(5) aryl or arylalkyl wherein said aryl is optionally substituted with 1 to 3 groups independently selected from $R^f$.
(6) trifluoromethyl $R_8$ is (1) H,
(2) OH, or
(3) $NH_2$ $R_9$ is (1) H, or
(2) OH;

$R_{10}$ is (1) $C(O)OR^b$,
(2) $C(O)N(OR^b)R^c$,
(3) $C(O)NR^cR^d$,
(4) $NHC(O)OR^b$,
(5) $NHC(O)NR^cR^d$,
(6) $CH_2OR^a$,
(7) $CH_2OCO_2R^b$,
(8) $CH_2OC(O)NR^cR^d$,
(9) $C(O)NR^cNR^cR^d$, or
(10) $C(O)NR^cSO_2R^b$;

$R^a$ is (1) hydrogen,
(2) optionally substituted alkyl,
(3) optionally substituted alkenyl,
(4) optionally substituted alkynyl,
(5) optionally substituted alkanoyl,
(6) optionally substituted aroyl,
(7) optionally substituted cycloalkanoyl,
(8) optionally substituted cycloalkenoyl,
(9) optionally substituted alkylsulfonyl
where the substituents on the alkyl, alkenyl, alkynyl, alkanoyl, aroyl, cycloalkanoyl, cycloalkenoyl, and alkylsulfonyl, are from 1 to 5 groups independently selected from hydroxy, alkoxy, aryl alkoxy, $NR^gR^h$, $CO_2R^b$, $CONR^cR^d$ and halogen,
(10) trifluoromethyl,
(11) arylsulfonyl optionally substituted with 1 to 3 groups independently selected from methyl, trifluoromethyl and halogen,
(12) a 5- or 6-member heterocycle containing 1 to 4 heteroatoms selected from oxygen, sulfur and nitrogen optionally substituted by 1 to 4 groups independently selected from methyl, trifluoromethyl, $C(O)NR^cR^d$, $CO_2R^b$ and halogen, and which may be saturated or partly unsaturated;

$R^b$ is (1) H,
(2) optionally substituted aryl,
(3) optionally substituted alkyl,
(4) optionally substituted alkenyl,
(5) optionally substituted alkynyl,
(6) optionally substituted cycloalkyl,
(7) optionally substituted cycloalkenyl, or
(8) optionally substituted 5- to 6-member
heterocycle containing from 1 to 4 heteroatoms independently selected from oxygen, sulfur and nitrogen; where the substituents on the aryl, alkyl, alkenyl, cycloalkyl, cycloalkenyl, heterocycle, or alkynyl are from 1 to 10 groups independently selected from
(i) hydroxy,
(ii) alkyl,
(iii) oxo,
(iv) $SO_2NR^gR^h$,
(v) arylalkoxy,
(vi) hydroxyalkyl,
(vii) alkoxy,
(viii) hydroxy alkoxy,
(ix) amino alkoxy,
(x) cyano,
(xi) alkyl-$S(O)_m$,
(xii) cycloalkyl optionally substituted with 1 to 4 groups independently selected from $R^e$,
(xiii) cycloalkenyl,
(xiv) halogen,
(xv) alkanoyloxy,
(xvi) $C(O)NR^gR^h$,
(xvii) $CO_2R^i$,
(xvii) —$NR^gR^h$,
(xix) 5 to 6-member heterocycle, which may be saturated or partially unsaturated, containing from 1 to 4 heteroatoms independently selected from oxygen, sulfur and nitrogen, and optionally substituted with 1 to 5 groups independently selected from $R^e$,
(xx) optionally substituted aryl, wherein the aryl substituents are 1,2-methylenedioxy or 1 to 5 groups independently selected from $R^e$,
(xxi) optionally substituted aryl alkoxy, wherein the aryl substituents are 1,2-methylenedioxy or 1 to 5 groups independently selected from $R^e$, and
(xxii) perfluoroalkyl;

$R^e$ is (1) halogen,
(2) alkyl,
(3) perfluoroalkyl,
(4) —S(O)$_m$R$^i$,
(5) cyano,
(6) R$^i$O(CH$_2$)$_v$—,
(7) R$^i$CO2(CH$_2$)$_v$—,
(8) R$_{10}$CO(CH$_2$)$_v$—,
(9) optionally substituted aryl where the substituents are from 1 to 3 of halogen, alkyl, alkoxy, or hydroxy,
(10) SO$_2$NR$^g$R$^h$, or
(11) amino;

$R^f$ is (1) methyl,
(2) X—C$_1$-C$_2$ alkyl, where X is O or S(O)$_m$,
(3) trifluoromethyl,
(4) NY$^1$Y$^2$, where Y$^1$ and Y$^2$ are independently H or methyl,
(5) hydroxy,
(6) halogen, and
(7) acetylamino, $R^g$ and $R^h$ are independently
(1) hydrogen,
(2) alkyl optionally substituted with hydroxy, amino, or CO$_2$R$^i$
(3) aryl optionally substituted with halogen, 1,2-methylenedioxy, alkoxy, alkyl or perfluoroalkyl,
(4) arylalkyl, wherein the aryl is optionally substituted with perfluorolkyl or 1,2-methylenedioxy;
(5) alkoxycarbonyl,
(6) alkanoyl,
(7) alkanoylalkyl,
(9) arylalkoxycarbonyl,
(10) aminocarbonyl,
(11) monoalkylaminocarbonyl
(12) dialkylaminocarbonyl; or $R^g$ and $R^h$ together with the N to which they are attached form a 5- to 6-membered ring containing 0 to 2 additional heteroatoms selected from O, S(O)$_m$, and N, optionally substituted with 1 to 3 groups independently selected from $R^e$ and oxo;

$R^i$ is (1) hydrogen,
(2) perfluoroalkyl,
(3) alkyl,
(4) optionally substituted aryl or arylalkyl, where the aryl substituents are from 1 to 3 groups independently selected from halogen, alkyl, alkoxy, and hydroxy; and all other variables are as defined under Formula I. In another aspect of the present invention there are provided compounds having the formula

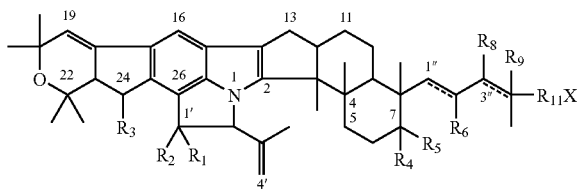

where R$_1$—R$_6$, R$_8$ and R$_9$ are as defined under Formula I, and R$_{11}$ is (1) COCl,
(2) CON$_3$, or
(3) NCO.

Most especially preferred are spot-on compositions, wherein the composition comprises nodulisporic acid derivatives which are nodulisporamides, which are compounds of the formula

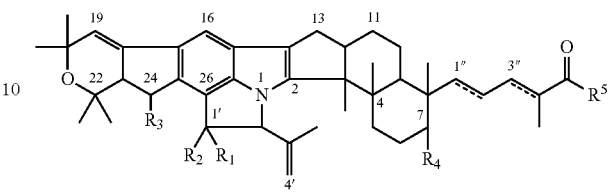

R$_1$ is
(1) hydrogen,
(2) optionally substituted C$_1$-C$_{10}$ alkyl
(3) optionally substituted C$_2$-C$_{10}$ alkenyl,
(4) optionally substituted C$_2$-C$_{10}$ alkynyl,
(5) optionally substituted C$_3$-C$_8$ cycloalkyl,
(6) optionally substituted C$_5$-C$_8$ cycloalkenyl
where the substituents on the alkyl, alkenyl, alkynyl, cycloalkyl and cycloalkenyl are 1 to 3 groups independently selected from C$_1$-C$_5$ alkyl, C$_1$-C$_{10}$ alkoxy, C$_1$-C$_{10}$ alkylthio, C$_1$-C$_{10}$ alkylsulfonyl, C$_3$-C$_8$ cycloalkyl, hydroxy, halogen, cyano, carboxy, amino, C$_1$-C$_{10}$ monoalkylamino, C$_1$-C$_{10}$ dialkylamino, C$_1$-C$_{10}$ alkanoyl amino and benzoyl amino wherein said benzoyl is optionally substituted with 1 to 3 groups independently selected from C$_1$-C$_4$ alkyl, C$_1$-C$_4$ alkoxy, C$_1$-C$_4$ alkylthio, C$_2$-C$_4$ alkenyl, C$_2$-C$_4$ alkynyl, C$_1$-C$_3$-perfluoroalkyl, amino, hydroxy, halogen, C$_1$-C$_5$ monoalkylamino, C$_1$-C$_5$ dialkylamino and C$_1$-C$_5$ alkanoyl amino,
(7) phenyl C$_0$-C$_5$ alkyl wherein said phenyl is optionally substituted with 1 to 3 groups independently selected from C$_1$-C$_4$ alkyl, C$_1$-C$_4$ alkoxy, C$_1$-C$_4$ alkylthio, C$_2$-C$_4$ alkenyl, C$_2$-C$_4$ alkynyl, C$_1$-C$_3$ perfluoroalkyl, amino, hydroxy, carboxy, halogen, C$_1$-C$_5$ monoalkylamino, C$_1$-C$_5$ dialkylamino and C$_1$-C$_5$ alkanoyl amino,
(8) C$_1$-C$_5$ perfluoroalkyl,
(9) a 5- or 6-member ring selected from morpholino, pyridyl and piperazino, optionally substituted by 1 to 3 groups independently selected from hydroxy, oxo, C$_1$-C$_{10}$ alkyl and halogen, R$^2$, R$^3$, and R$^4$ are independently OR$^a$, OCO$_2$R$^b$, OC(O) NR$^c$R$^d$; or
R$^1$ and R$^2$ together represent =O, =NOR$^a$ or =N—NR$^c$R$^d$;
R$^5$ is NR$^c$R$^d$,
$R^a$ is
(1) hydrogen,
(2) optionally substituted C$_1$-C$_{10}$ alkyl,
(3) optionally substituted C$_3$-C$_{10}$ alkenyl,
(4) optionally substituted C$_3$-C$_{10}$ alkynyl,
(5) optionally substituted C$_1$-C$_{10}$ alkanoyl,
(6) optionally substituted C$_1$-C$_{10}$ alkenoyl,
(7) optionally substituted C$_1$-C$_{10}$ alkynoyl,
(8) optionally substituted benzoyl,
(9) optionally substituted phenyl,
(10) optionally substituted C$_1$-C$_7$ cycloalkanoyl,
(11) optionally substituted C$_4$-C$_7$ cycloalkenoyl,
(12) optionally substituted C$_1$C$_{10}$ alkylsulfonyl
(13) optionally substituted C$_3$-C$_8$ cycloalkyl
(14) optionally substituted C$_5$-C$_8$ cycloalkenyl
where the substituents on the alkyl, alkenyl, alkynyl, alkanoyl, alkenoyl, alkynoyl, benzoyl, phenyl, cycloalkanoyl, cycloalkenoyl, alkylsulfonyl, cycloalkyl and cycloalkenyl are from 1 to 5 groups independently selected from hydroxy, $C_1$-$C_6$ alkoxy, $C_3$-$C_7$ cycloalkyl, aryl $C_1$-$C_3$ alkoxy, $NR^gR^h$, $CO_2R^b$, $CONR^cR^d$ and halogen,
(15) $C_1$-$C_5$ perfluoroalkyl,
(16) phenylsulfonyl optionally substituted with 1 to 3 groups independently selected from $C_1$-$C_5$ alkyl, $C_1$-$C_5$ perfluoroalkyl, nitro, halogen or cyano,
(17) a 5- or 6-member ring selected from piperidino, morpholino, pyridyl and piperazino optionally substituted by 1 to 4 groups independently selected from $C_1$-$C_5$ alkyl, $C_1$-$C_5$ alkenyl, $C_1$-$C_5$ perfluoroalkyl, amino, $C(O)R^cR^d$, cyano, $CO_2R^b$ or halogen;

$R^b$ is
(1) H,
(2) optionally substituted phenyl,
(3) optionally substituted $C_1$-$C_{10}$ alkyl,
(4) optionally substituted $C_3$-$C_{10}$ alkenyl, or
(5) optionally substituted $C_3$-$C_{10}$ alkynyl,
where the substituents on the phenyl, alkyl, alkenyl or alkynyl are from 1 to 5 groups independently selected from hydroxy, $C_1$-$C_6$ alkoxy, $C_3$-$C_7$ cycloalkyl, halogen, $C_1$-$C_5$ alkanoyloxy, $C(O)NR^cR^d$, $CO_2R^b$, formyl, —$NR^gR^h$, optionally substituted phenyl, and optionally substituted phenyl $C_1$-$C_3$ alkoxy, wherein the phenyl substituents are 1 to 3 groups independently selected from $R^e$;

$R^c$ and $R^d$ are independently $R^b$; or
$R^c$ and $R^d$ together with the N to which they are attached form a piperidino, morpholino or piperazino optionally substituted with 1 to 3 groups independently selected from $R^g$ and oxo;

$R^e$ is
(1) halogen,
(2) $C_1$-$C_7$ alkyl,
(3) $C_1$-$C_3$ perfluoroalkyl,
(4) —$S(O)_mR^i$,
(5) cyano,
(6) nitro,
(7) $R^jO(CH_2)_v$—,
(8) $R^jCO_2(CH_2)_v$—,
(9) $R^jOCO(CH_2)_v$—,
(10) optionally substituted phenyl where the substituents are from 1 to 3 halogen, $C_1$-$C_6$ alkyl, $C_1$-$C_6$ alkoxy, or hydroxy;

v is 0 to 3;

$R^g$ and $R^h$ are independently
(1) hydrogen,
(2) $C_1$-$C_6$ alkyl,
(3) aryl,
(4) aryl $C_1$-$C_6$ alkyl,
(5) $C_1$-$C_5$ alkoxycarbonyl,
(6) $C_1$-$C_5$ alkylcarbonyl, or
(7) $C_1$-$C_5$ alkanoyl $C_1$-$C_5$ alkyl; or $R^g$ and $R^h$ together with the N to which they are attached form a piperidino, morpholino or piperazino optionally substituted with 1 to 3 groups independently selected from $R^g$ and oxo;

$R^i$ and $R^j$ are independently
(1) hydrogen,
(2) $C_1$-$C_3$ perfluoroalkyl,
(3) optionally substituted $C_1$-$C_6$ alkyl, where the substituents are aryl or substituted phenyl;
(4) phenyl or substituted phenyl where the substituents are from 1 to 3 groups independently selected from halogen, $C_1$-$C_6$ alkyl, $C_1$-$C_6$ alkoxy, or hydroxy;

m is 0 to 2; or a pharmaceutically acceptable salt thereof.

Most especially preferred are compounds of the formula

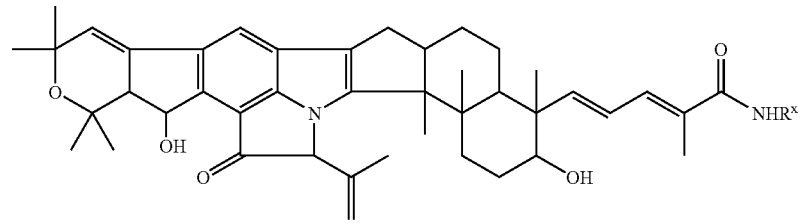

wherein $R^x$ is selected from the group consisting of:
H, $CH_3$, $CH_2CH_3$, $C(CH_3)_3$, $CH_2CH_2CH_3$, $CH_2CH_2OH$, $CH(CO_2CH_3)CH_2OH$, $CH_2CO_2CH_3$, $CH_2CH(OCH_2CH_3)_2$, $CH_2CH_2OCH_2CH_2OH$, $CH(CH_3)(CH_2)_3C(CH_3)_2OH$, $(CH_2)_3OH$, $(CH_2)_4OH$, $(CH_2)SOH$, $CH(CH_2OH)CH_2CH_3$, $NHC(CH_3)_3$, $CH_2CN$, $(CH_2)_6OH$, $CH_2CH(OH)CH_3$, $CH(CH_2OH)CH_2CH_3$, $CH_2CH_2SCH_3$, $CH_2CH_2SCH_2CH_3$, $CH_2CONH$, $CH(CH_3)(CH_2OH)_2$, $CH_2CH_2NHCH_2CH_2OH$, $CH(CH_2OH)(CH_2)_3CH_3$, $CH(CH_2OCH_3)CH_3$, $(CH_2)_2SH$, $(CH_2)_4NH_2$, $CH_2CH_2SO_2CH_3$, $CH_2CH_2S(O)CH_3$, $CH(CH(CH_3)_2)CH_2OH$, $(CH_2)_3NH_2$, $(CH_2)_3N(CH_2CH_3)_2$, $(CH_2)_3N(CH_3)_2$, $OCH_2CH_3$, $CH_2CH(OH)CH_2OH$, $OCH_3$, $CH_2CH_2OCH_3$, $CH_2CH_2NHC(O)CH_3$, $C(CH_3)_2CH_2OH$, $c$-$C_3H_5$, $c$-$C_6H_{11}$, $(CH_2)_3OCH_2CH_3$, $CH_2CH=CH_2$, $C(CH_2CH_3)(CH_2OH)_2$, $CH_2C\equiv CH$, $CH_2CO_2CH_2CH_3$, $CH_2CH_2F$, $(CH_2)_{11}CH_3$, $CH_2CH_2N(CH_3)_2$, $CH_2CH_2OCH_2CH_2NH_2$, $CH_2CF_3$, $NHCH_2CO_2CH_2CH_3$, $CH(CH_3)CO_2CH_3$, $C(CH_3)_2CH_2C(O)CH_3$, $CH(CO_2CH_2CH_3)_2$, $CH_2CH_3$, $CH(CH_2CH_2CH_3)CO_2CH_3$, $CH_2CH_2CH_2OCH_3$, $C(CH_3)_2C\equiv CH$, $(CH_2)_4CH_3$, $CH(CH_2CH_2CH_3)_2$, $(CH_2)_5CH_3$, $CH_2CH_2CO_2H$, $CH(CH(CH_3)_2)CO_2CH_3$, $OCH_2CO_2H$, $CH(CH(CH_3)_2)CH_2OH$, $CH(CH(CH_3)_2)CH_2OH$, $CH(CH_3)CH_2OH$, $CH(CH_3)CH_2OH$, $CH(CH_3)_2$, $C(CH_3)_3$, $(CH_2)CH(CH_3)_2$, $CH(CH_3)CH_2CH_3$, $CH_2CH(CH_3)OH$, $(CH_2)_2CH_3$, $(CH_2)_2OCH_2CH_3$, 1-adamantyl, $(CH_2)_8CH_3$, $CH(CH_3)CH(CH_3)_2$, $(CH_2)_3NHCH_3$, $(CH_2)_2N(CH_2CH_3)_2$,

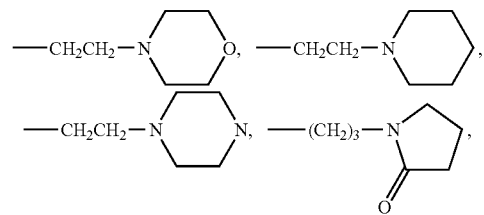

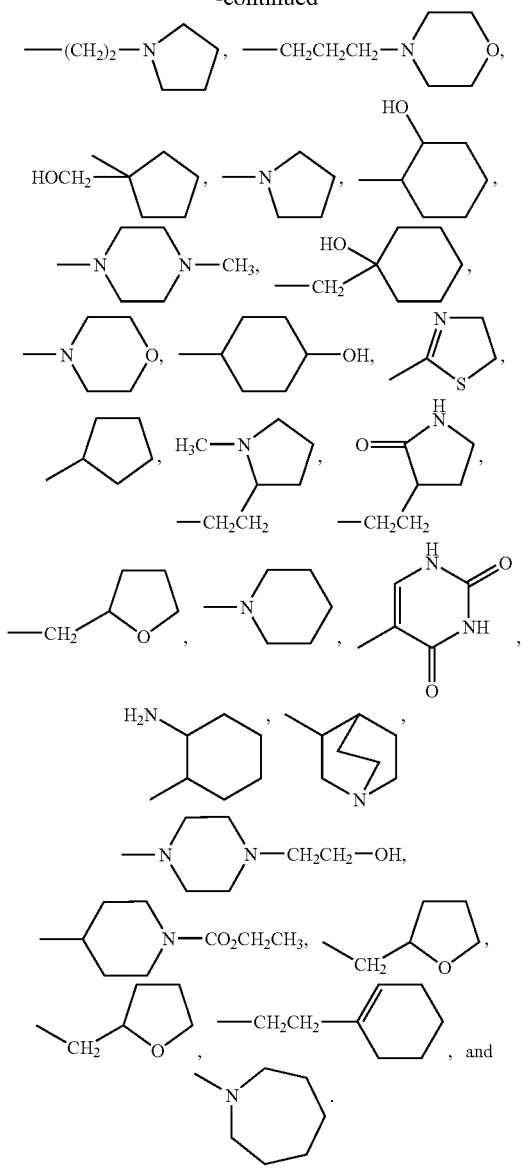

A most especially preferred nodulisporamide derivative is one wherein $R^X$ is hydrogen.

Other antibiotics may also be used as a bioactive agent in the practice of this invention.

The bioactive agent can be, for example a peptide or protein. The biologically-active agent may also be a substance, or metabolic precursor thereof, which is capable of promoting growth and survival of cells and tissues, or augmenting the activity of functioning cells, as for example, blood cells, neurons, muscle, bone marrow, bone cells and tissues, and the like. For example, the biologically-active agent may be a nerve growth promoting substance, as for example, a ganglioside, phosphatidylserine, a nerve growth factor, brain-derived neurotrophic factor, a fibroblast growth factor, and the like. To promote tissue growth, the biologically-active agent may be either a hard or soft tissue promoting substance or combinations thereof. Suitable tissue growth promoting agents include, for example, fibronectin (FN), endothelial cell growth factor (ECGF), cementum attachment extracts (CAE), human growth hormone (HGH), a Periodontal ligament cell growth factor, fibroblast growth factor (FGF), animal growth hormones, platelet derived growth factor (PDGF), epidermal growth factor (EGF), protein growth factor interleukin-1 (IL-1), transforming growth factor (TGF.beta.-2), insulin-like growth factor II (ILGF-II), human alpha thrombin (HAT), osteoinductive factor (OIF), bone morphogenetic protein (BMP) or protein derived therefrom, demineralized bone matrix, and releasing factors thereof. Further, the agent may be a bone growth promoting substance such as hydroxyapatite, tricalcium phosphate, a di- or polyphosphonic acid, an anti-estrogen, a sodium fluoride preparation, a substance having a phosphate to calcium ratio similar to natural bone, and the like. A bone growth promoting substance may be in the form, as for example, of bone chips, bone crystals or mineral fractions of bone and/or teeth, a synthetic hydroxyapatite, or other suitable form. The agent may further be capable of treating metabolic bone disorders such as abnormal calcium and phosphate metabolism by, for example, inhibiting bone resorption, promoting bone mineralization, or inhibiting calcification. See, for example, U.S. Pat. No. 4,939,131 to Benedict et al., U.S. Pat. No. 4,942,157 to Gall et al., U.S. Pat. No. 4,894,373 to Young, U.S. Pat. No. 4,904,478 to Walsdorf et al., and U.S. Pat. No. 4,911,931 to Baylink, U.S. Pat. No. 4,916,241 to Hayward et al., U.S. Pat. No. 4,921,697 to Peterlik et al., U.S. Pat. No. 4,902,296 to Bolander et al., U.S. Pat. No. 4,294,753 to Urist, U.S. Pat. No. 4,455,256 to Urist, U.S. Pat. No. 4,526,909 to Urist, U.S. Pat. No. 4,563,489 to Urist, U.S. Pat. No. 4,596,574 to Urist, U.S. Pat. No. 4,619,989 to Urist, U.S. Pat. No. 4,761,471 to Urist, U.S. Pat. No. 4,789,732 to Urist, U.S. Pat. No. 4,795,804 to Urist, and U.S. Pat. No. 4,857,456 to Urist, the disclosures of which are incorporated by reference herein. Other biologically active peptides and proteins include depsipeptides which act at the neuromuscular function by stimulating presynaptic receptors belonging to the secretin receptor family resulting in the paralysis and death of parasites. A preferred depsipeptide is emodepside. These depsipeptides can also be combined with a pyrazinoisoquinoline compound with a preferred embodiment being emodepside and praziquantel.

Further still, the bioactive agent can be an antineoplastic, antitumor or anticancer agent. Examples include but are not limited to Erbitux, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel, γ-radiation, alkylating agents including nitrogen mustard such as cyclophosphamide, ifosfamide, trofosfamide, chlorambucil, nitrosoureas such as carmustine (BCNU), and lomustine (CCNU), alkylsulphonates such as busulfan, and treosulfan, triazenes such as dacarbazine, platinum containing compounds such as cisplatin and carboplatin, plant alkaloids including vinca alkaloids, vincristine, vinblastine, vindesine, and vinorelbine, taxoids including paclitaxel, and docetaxol, DNA topoisomerase inhibitors including epipodophyllins such as etoposide, teniposide, topotecan, 9-aminocamptothecin, campto irinotecan, and crisnatol, mitomycins such as mitomycin C, anti-metabolites, including anti-folates such as DHFR inhibitors, methotrexate and trimetrexate, IMP dehydrogenase inhibitors including mycophenolic acid, tiazofurin, ribavirin, EICAR, ribonuclotide reductase inhibitors such as hydroxyurea, deferoxamine, pyrimidine analogs including uracil analogs 5-fluorouracil, floxuridine, doxifluridine, and ratitrexed, cytosine analogs such as cytarabine (ara C), cytosine arabinoside, and fludarabine, purine analogs such as mercaptopurine, thioguanine, hormonal therapies including receptor antagonists, the anti-estrogens tamoxifen, raloxifene and megestrol, LHRH agonists such as goscrclin, and leuprolide acetate, anti-androgens such as flutamide, and bicalutamide, retinoids/deltoids, Vitamin D3 analogs including EB 1089, CB 1093, and KH 1060, photodyamic therapies including vertoporfin (BPD-MA), phthalocyanine, photosensitizer Pc4, Demethoxy-hypocrellin A, (2BA-2-DMHA), cytokines including Interferon, α-Interferon, γ-interferon, tumor necrosis factor, as well as other compounds having anti-tumor activity including isoprenylation inhibitors such as lovastatin, dopaminergic neurotoxins such as 1-methyl-4-phenylpyridinium ion, cell cycle inhibitors such as staurosporine, alsterpaullone, butyrolactone I, Cdk2 inhibitor, Cdk2/Cyclin Inhibitory Peptide I, Cdk2/Cyclin Inhibitory Peptide II, Compound 52 [2-(2-hydroxyethylamino)-6-(3-chloroanilino)-9-isopropylpurine], Indirubin-3'-monoxime, kenpaullone, olomoucine, Iso-olomoucine, $N^9$-isopropyl-olomoucine, purvalanol A, roscovitine, (S)-isomer roscovitine and WHI-P180 [4-(3'-hydroxyphenyl)amino-6,7-dimethoxyquinazoline, actinomycins such as actinomycin D and dactinomycin, bleomycins such as bleomycin A2, bleomycin B2, and peplomycin, anthracyclines such as daunorubicin, doxorubicin (adriamycin), idarubicin, epirubicin, pirarubicin, zorubicin, and mitoxantrone, MDR inhibitors including verapamil, and $Ca^{2+}$ ATPase inhibitors such as thapsigargin.

The biologically-active agent may be included in the compositions in the form of, for example, an uncharged molecule, a molecular complex, a salt, an ether, an ester, an amide, or other form to provide the effective biological or physiological activity. The term "pharmaceutical agent" or "therapeutic agent" also includes the pharmaceutically or veterinary acceptable acid or base salts, where applicable, of these compounds. The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinary acceptable aliphatic, alicyclic and aromatic carboxylic acids, dicarboxylic acids tricarboxylic acids and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

The ester and amide derivatives of these compounds, where applicable, are also contemplated. Specific compounds which belong to these classes of therapeutic agents are well known to the practitioner of this art.

In one embodiment of the invention the subcutaneously volatile solvent is selected from a group which includes but is not limited to alcohols, aldehydes, ketones, ethers, esters, amides and mixtures thereof. Advantageous subcutaneously volatile solvents include ethanol, 1-propanol, 2-propanol, 1-butanol, 2-butanol, 1-pentanol, 2-pentanol, 3-pentanol, propylene glycol, PEG 200, PEG 300, PEG 400, diethylene glycol ethyl ether, isopropylidene glycerol, dimethyl isosorbide, propylene carbonate, glycerol, acetone, N-methyl-pyrrolidone, N-pyrrolidone, methylethylketone (MEK), dimethylsulfoxide (DMSO), 1-dodecylazacycloheptane, dipropyleneglycol methyl ether, methyl acetate, ethyl acetate, ethyl lactate, dimethylformamide, N,N-diethyl-m-toluamide, dimethylacetamide, ethylacetamide, tetrahydrofuran, caprolactam, decylmethylsulfoxide, triacetin and mixtures thereof. An even more advantageous subcutaneously volatile solvent is the group selected from the group consisting of glycerol, N-methylpyrrolidone (NMP), triacetin, dimethylacetamide, ethylacetamide, ethyl acetate and mixtures thereof.

In one embodiment of the invention, the biologically acceptable polymer can be any biologically acceptable polymer, such as a biologically acceptable polymer recognized in documents cited herein. For instance, the biologically acceptable polymer can have one or more or all of the following characteristics: be bioerodible by cellular action, biodegradable by action of non-living body fluid components, soften when exposed to heat but return to the original state when cooled and are capable of substantially dissolving or dispersing in a water-miscible carrier or solvent to form a solution or dispersion. Upon contact with an aqueous fluid and the polymer are capable of assisting in the formation of the film coated or encapsulated liquid. The kinds of polymers suitable for the present composition generally include any having the foregoing characteristics. Examples are polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malicacid), poly(amino acids), poly(methyl vinyl ether), poly(maleic anhydride), chitin, chitosan, and copolymers, terpolymers, or combinations or mixtures therein. Polylactides, polycaprolactones, polyglycolides and copolymers thereof are advantageous polymers, with poly (lactide-co-glycolide)copolymer ("PLGA") highly advantageous.

In an advantageous embodiment of the invention, when the bioactive polymer is PLGA, the ratio of PL to GA is about 60:40 to about 99:1. In a further advantageous embodiment of the invention, the bioactive polymer is PLGA, the ratio of PL to GA is about 70:30 to about 80:20. In a still further advantageous embodiment of the invention, the bioactive polymer is PLGA, the ratio of PL to GA is about 75:25.

An advantageous form for the above injectable formulations is where the bioactive agent is present in an amount of about 0.1 to about 10.0% w/v. Even more advantageous are injectable formulations wherein the bioactive agent is present in an amount of about 0.5 to about 5.0% w/v. Especially advantageous are injectable formulations wherein the bioactive agent is present in an amount of about 0.5 to about 1.0% w/v. An especially advantageous amount for cattle products is where the bioactive agent is present in an amount of about 4% to about 6%, even more advantageously, about 5%.

Alternatively, the amount of bioactive agent for the above injectable formulations can also be measured by the amount of bioactive agent per weight of the mammal being treated. In this embodiment of the invention, the amount of bioactive agent can range from about 0.01 to about 100 mg/kg, where mg refers to the weight of the bioactive agent and kg refers to the weight of the mammal being treated. In an advantageous embodiment of the invention, the amount of bioactive agent ranges from about 0.05 mg/kg to about 10 mg/kg. In a particularly advantageous embodiment of the invention, the amount of bioactive agent ranges from about 0.1 mg/kg to about 5 mg/kg.

Since it is advantageous to have a ready to inject formulation as part of the invention, the amount of bioactive agent can also be measured by the amount of bioactive agent present in a unit of volume of injectable formulation. In this embodiment of the invention, the amount of bioactive agent can range from about 0.01 mg/mL to about 100 mg/mL. In an advantageous embodiment of the invention, the amount of bioactive agent ranges from about 0.1 mg/mL to about 50 mg/mL. In a particularly advantageous embodiment of the invention, the amount of bioactive agent ranges from about 5 mg/mL to about 50 mg/mL.

An advantageous embodiment of the invention is a long-acting injectable formulations wherein
(a) the bioactive agent is an avermectin, milbemycin or mixture thereof;
(b) the subcutaneously volatile solvent or mixture of subcutaneously volatile solvents,
(c) the biologically acceptable polymer is PLGA;
(d) optionally, at least one bioactive acceptable additive or excipient; and
(e) optionally, an antioxidant.

An advantageous form of the above embodiment of the invention is where the avermectin or milbemycin is selected from the group consisting of eprinomectin, ivermectin, and moxidectin.

The long-acting injectable formulation of the present invention may be prepared by adding (i) dissolving the biologically acceptable polymer in a subcutaneously volatile solvent to form a solution; (ii) adding a therapeutically effective amount of a bioactive agent to the solution to form the formulation.

The instant formulation is equally applicable to other compounds used for injection as long as such compounds are soluble in the mixture of the subcutaneously volatile solvent and biologically acceptable polymer. Additional compounds that can be used in this formulation are other antiparasitic agents and antibiotics, therapeutic vitamin and mineral supplements, and other agents that are assisted in their therapeutic effect by having their effects extended over a prolonged period of time. Again, such compounds would be well known to the practitioner.

The long acting injectable formulations of the invention are used to control pests in mammals, birds and fish. Particular examples of mammals include humans, cattle, horses, pigs, sheep, dogs and cats. Examples of the pests that may be controlled by the active ingredient are generally described in European Patent Application EP-A-0 295 117 and Hatton et al U.S. Pat. No. 5,232,940, incorporated by reference herein in its entirety and relied upon. Illustrative of specific parasites of various host animals which may be controlled by the present invention include arthropods such as mites (e.g., mesostigmatids, itch, mange, scabies, chiggers), ticks (e.g., soft-bodied and hard-bodied), lice (e.g., sucking, biting), fleas (e.g., dog flea, cat flea, oriental rat flea, human flea), true bugs (e.g., bed bugs, Triatomid bugs), bloodsucking adult flies (e.g., horn fly, horse fly, stable fly, black fly, deer fly, louse fly, tsetse fly, mosquitoes), and parasitic fly maggots (e.g, bot fly, blow fly, screwworm, cattle grub, fleeceworm); helminths such as nematodes (e.g., threadworm, lungworm, hookworm, whipworm, nodular worm, stomach worm, round worm, pinworm, heartworm), cestodes (e.g., tapeworms) and trematodes (e.g., liver fluke, blood fluke); protozoa such as coccidia, trypanosomes, trichomonads, amoebas and plasmodia; acanthocephalans such as thorny-headed worms (e.g., lingulatulida); and pentastomids such as tongueworms.

Advantageously, the injectable formulations of the invention are directed toward the treatment of nematodes in cattle, sheep and pigs. Even more advantageously, the nematodes are selected from the group consisting of *Cooperia oncophora/surnabada; Cooperia pectinata; Cooperia punctata; Ostertagia ostertagi/lyrata; Ostertagia circumcincta, Trichuris suis, Oesophagostumum* spp., *Haemonchus contortus, Haemonchus phacei, Trichostronglyus axei, Trichostronglyus columbriformis* and mixtures thereof. Surprisingly, the injectable formulations of the invention also display efficacy against macrolide resistant strains of nematodes. A particularly advantageous aspect of this invention is where the method of treating nematodes is directed against macrolide resistant *Ostertagia*.

The very high effectiveness of the method and of the composition according to the invention shows not only high instantaneous effectiveness but also an effectiveness of very long duration after the treatment of the animal. In one embodiment of the invention, the effectiveness of the long acting injectable formulations of the invention against pests is from about 1 day to about 60 days. In advantageous embodiment of the invention, the effectiveness of the long acting injectable formulations of the invention against pests is from about 1 day to about 120 days. In the context of commercial mammals such as cattle, pigs or sheep, about 120 days represents a season long treatment.

In a further advantageous embodiment of the invention, the effectiveness of the long acting injectable formulations of the invention against pests is from about 1 day to about 180 days. In a still further advantageous embodiment of the invention, the effectiveness of the long acting injectable formulations of the invention against pests is from about 1 day to about 365 days.

Due to the exquisite sensitivity of certain nematodes such as the heartworm (*Dirofilaria immitis*) relatively low levels of active agent provide high levels of efficacy allowing for protection against heartworm disease for periods of time of up to a year after treatment.

In another embodiment of the invention, the method of treating pests with the long acting injectable formulations comprises of injecting the formulation subcutaneously into the mammal. In an advantageous embodiment of the invention, the location of the subcutaneous administration is at the base of the ear or in the neck cranial to the shoulder of the mammal.

The long acting injectable formulations of the invention are also surprising in that they are suitable as ready to use formulations. A problem of other long acting injectable formulations is a requirement for reconstitution/suspension prior to administration or the fact they are only available as solid dosage forms. In these cases, a larger needle size becomes necessary to administer the long acting injectable formulation. Needle gauge numbers are inversely proportional to the diameter of the needle, i.e. a larger needle gauge represents a needle with a smaller diameter. Needle gauge sizes for use in mammals are commonly of gauge 18-22 in small mammals and gradually increasing in size as the size of the mammal increases (e.g. gauge 16 for cattle). Surprisingly, the long acting injectable formulation of the invention allows for needles with larger needle gauges. In one advantageous embodiment of the invention, the long acting injectable formulations of the invention can accommodate needle gauge of about 18 to about 24 in adult mammals and about 24 to about 30 in newborn mammals.

The invention will now be further described by way of the following non-limiting examples. It is not to be construed as a limitation of the invention.

EXAMPLES

Example 1

Study of Eprinomectin Plasma Concentration in Cattle after Injection Behind the Ear The plasma levels of eprinomectin (B1a) in cattle treated with eprinomectin when administered subcutaneously on the back of the ear at 1.0 mg/kg body weight as a long-acting solution and the preventive efficacy against induced infection of infective $3^{rd}$ stage (L3) nematode larvae 120 days after treatment were evaluated.

Five replicates of four cattle each were formed based on decreasing Day—1 bodyweights. Within replicates, cattle were randomly allocated to Treatment Group 1, 2, 3 or 4:
Group 1—vehicle (control) at 1 mL/50 kg body weight;
Group 2—eprinomectin 5% w/v 5% PLGA LAI solution at 1 mL/50 kg body weight (1.0 mg/kg) administered caudal to the ear;
Group 3—eprinomectin 10% w/v 5% PLGA LAI solution at 1 mL/100 kg body weight (1.0 mg/kg) administered caudal to the ear;
Group 4—eprinomectin 5% w/v 5% PLGA (low molecular weight) LAI solution at 1 mL/50 kg body weight (1.0 mg/kg) administered in front of the shoulder.
Treatments were administered once by subcutaneous injection on Day 0 on the back of the right ear—Groups 1, 2, and 3—or in front of the right shoulder—Group 4. The location in the back of the right ear was the loose tissue just distal to the lower end of the auricular cartilage. The appropriate dose volume for each animal was administered by subcutaneous injection using a sterile 5 mL-syringe fitted with a 19G×1¼ inch hypodermic needle to ensure subcutaneous delivery. When necessary, does volumes were rounded to the next 0.1 mL above the calculated does as determined based on Day-1 individual body weights.

Blood samples were collected from all animals and plasma recovered on Days—14, 0 (prior to treatment) and then on Days 1, 2, 3, 4, 5, 6, 7, 14 and weekly thereafter until Day 140 and on Day 148. Plasma samples were assayed for eprinomectin B1a concentration.

Eprinomectin (B1a component) plasma levels were determined for each animal of Groups 2, 3, and 4 at each sampling time. Samples from Group 1, were assayed infrequently only to demonstrate absence of eprinomectin B1a. Mean plasma levels were calculated by treatment group for each time point.

Nematode counts for each species were transformed to ln (count+1) for calculation of geometric means for each treatment group. Efficacy was determined for each nematode species by calculating the percent efficacy as $100[(C-T)/C]$, where C is the geometric mean count among Vehicle-treated controls and T is the geometric mean count among eprinomectin LAI-treated animals. Treatment groups was compared to the Vehicle (Control) group using Wilcoxon Rank Sum Tests. A two-sided significance level of 0.05 was used.

Mean plasma eprinomectin B1a concentrations of Groups 2 and 3 were very similar with peak concentrations of 23.5 ng/mL or 22.0 ng/mL, respectively, observed on Day 2 followed by a continuous depletion until Day 126 (last assays). In Group 4 cattle, mean eprinomectin B1a concentrations peaked in plasma at 14.1 ng/mL on Day 1; a second peak was seen at 11.9 ng/mL on Day 63 followed by a continuous depletion until Day 126 (last assays). FIG. 1 presents a graphical representation of these results.

No injection site reaction was observed in any animal of any Group. All calves accepted the treatment well. No health problems were observed.

Example 2

Comparison of Effect of Injection Site on Plasma Concentration

Figure 4:
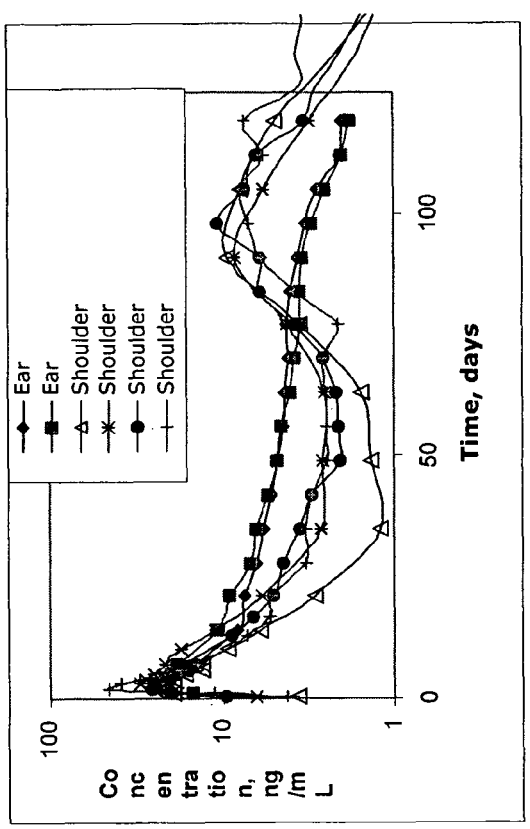
FIG. 4 shows a comparison of the eprinomectin plasma levels between ear and shoulder injection

The observed mean plasma concentration-time profiles and mean pharmacokinetic parameters for cattle treated at the base of the ear and these treated by injection in the neck or the shoulder are shown in Table 1 and FIG. 4.

TABLE 1

Comparison of data from Examples 1 and 2

| Injection Site | $AUC_{0-119\,d}$ day * ng/mL | $AUC_{0-\infty}$ day * ng/mL | $C_{max}$ ng/mL | $T_{max}$ day | Trough Conc. ng/mL | $C_{last}$ ng/mL | $T_{Last}$ day | $T_{1/2}$ day |
|---|---|---|---|---|---|---|---|---|
| Example 1 Ear | 700.0 ± 89.6 | 783.1 ± 102.9 | 24.8 ± 8.7 | 2.8 | NA | 1.99 | 119 | 27.1 |
| Example 2 Ear | 720.8 ± 160.2 | 789.4 ± 145.0 | 22.7 ± 6.3 | 3.0 | NA | 1.80 | 119 | 26.0 |
| Example 3 Neck | 767.2 ± 260.5 | 832.8 ± 233.3 | 30.6 ± 18.8 | 3.5 | 2.61 | 1.08 | 140 | 14.2 |
| Example 4 Neck | 623.4 ± 187.4 | 713.1 ± 153.0 | 25.2 ± 8.3 | 2.0 | 1.34 | 0.95 | 147 | 11.7 |
| Example 2 Shoulder | 715.5 ± 87.1 | 816.7 ± 66.5 | 27.3 ± 9.3 | 3.0 | 2.23 | 0.66 | 167 | 19.3 |
| Example 2 Shoulder | 694.0 ± 213.1 | 890.5 ± 157.8 | 46.8 ± 20.4 | 2.3 | 2.43 | 0.98 | 175 | 16.5 |
| P value | 0.4912 | 0.6528 | | | | | | 3.102E−06 |

$AUC_{0-119\,d}$ = Area Under the Curve, calculated by the linear trapezoidal method from day 0 to day 119
$AUC_{0-\infty}$ = Area Under the Curve, calculated by the linear trapezoidal method extrapolated to infinity
$C_{MAX}$ = Peak Concentration
$T_{max}$ = Time to Peak Concentration
Trough Conc. = approximate concentration at the plateau between the first and second concentration maximums
Clast = last quantifiable plasma concentration
Tlast = time to last quantifiable plasma concentration
$T_{1/2}$ = Terminal plasma half-life
P value = Probability that shoulder and ear parameters are statistically equivalent. Determined by two-sample equal variance t-test. P ≥ 0.05 (95% confidence) is defined as statistically equivalent.

After injection of eprinomectin LAI in the ear of cattle, mean maximum concentrations of between 23 and 25 ng/mL were observed from 1 to 7 days post-injection. Eprinomectin concentrations then declined multi-exponentially. Samples have currently been collected out to 119 days following injection. Area under the plasma concentration versus time curves from 0 to 119 days averaged 700.0 and 720.8 ng.day/mL for Example 1 Group 2 and Group 3 animals, respectively. Concentrations declined slowly between day 28 and day 81 with concentrations over this time period ranging from 6.9 to 3.9 ng/mL. Half-lives over this time period were 60.1 and 53.0 days for Example 1 Group 2 and 3, respectively. A faster decay occurred from day 98 to day 119 with half-lives ranging from 14 to 35 days. These shorter half-lives are somewhat longer with those determined following administration of eprinomectin LAI in the neck/shoulder of cattle. It should be noted however that the half-lives for these formulations may be indicative of the absorption of eprinomectin and the terminal half-life may not have been reached by day 119 in the ear injected cattle.

After injection of eprinomectin LAI in the shoulder of cattle mean maximum plasma concentrations of 25 to 47 ng/mL were observed 1 to 5 days post-injection. Plasma concentration versus time profiles differed significantly from those following injection to the ear. Plasma concentrations declined until approximately day 63 when a rise in plasma concentration occurred leading to a second maximum of between 8 and 10 ng/mL on day 91 to 98 of the study. Plasma concentrations then declined with average terminal plasma half-lives of 12 to 19 days. Plasma concentrations were below the limit of quantitation by day 189 of the study. Mean trough concentrations observed between day 28 and day 63 of the study were between 1.34 and 2.61 ng/mL.

AUCs between 0 and 119 days were compared between animals injected in the ear and those injected in the shoulder using an equal variance two sample t-test. No statistical difference was found between the AUCs following injection in the ear and injection in the shoulder indicating that the extent of absorption is unchanged by the location of administration. Similar results were obtained using AUCs extrapolated to infinity with less than 15% extrapolated for all animals. The plasma concentration versus time profile is, however, quite different between the two injection locations as can be seen in FIG. 4. Plasma concentrations following injection in the ear are on average higher than those following shoulder injection.

Example 3

Figure 5:
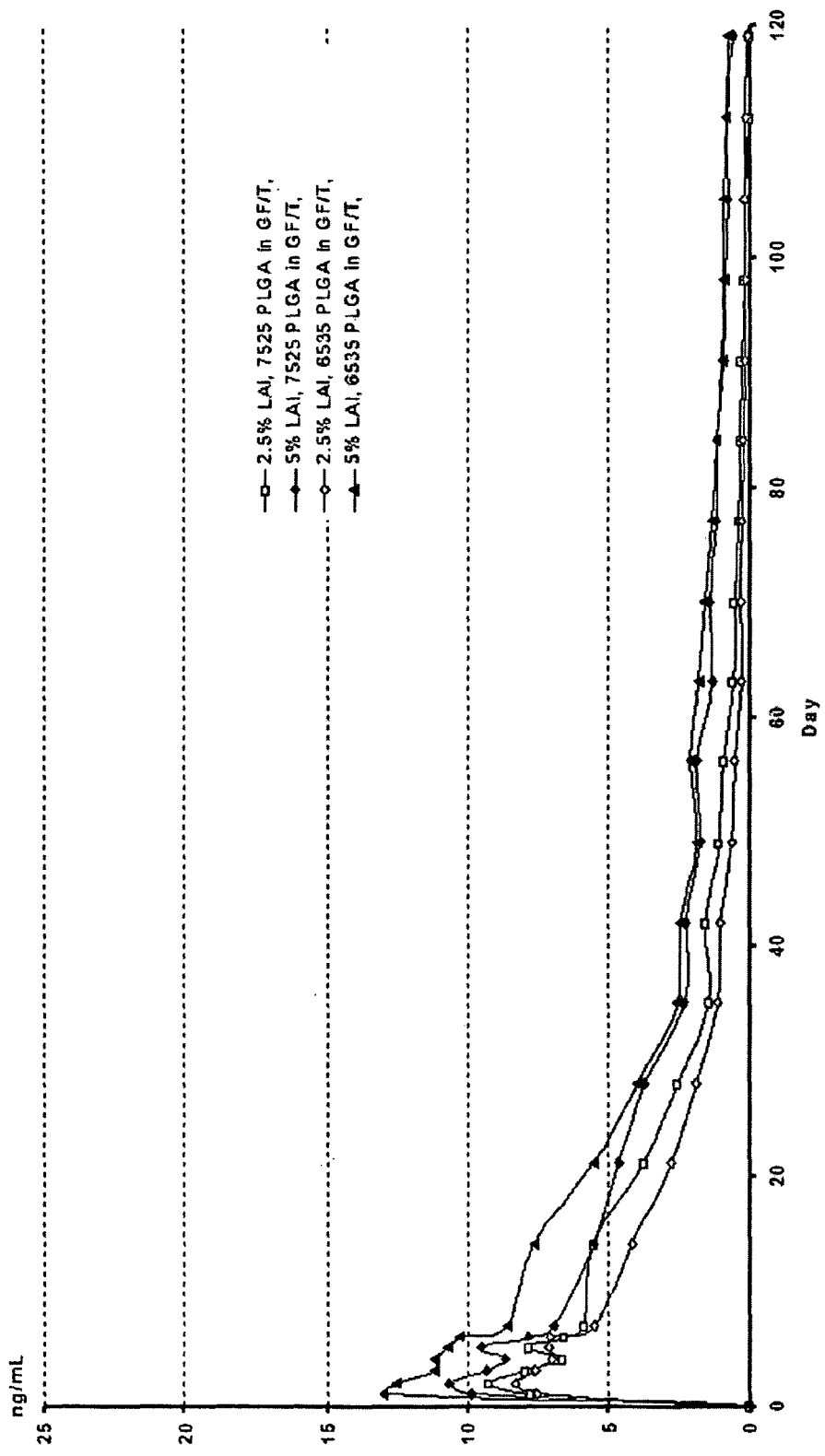
FIG. 5 shows the plasma depletion of emamectin after injection.

Study of Emamectin Plasma Concentration in Cattle Using Long Acting Injectable Formulations of the Invention The study of Example 1 was replicated using a formulation containing emamectin in place of eprinomectin. The results of this test are displayed in FIG. 5.

Example 4

Study of Moxidectin Plasma Concentration in Cattle Using Long Acting Injectable Formulations of the Invention The plasma levels of moxidectin in cattle treated with moxidectin when administered subcutaneously in front of the right shoulder at 1.0 mg/kg body weight as a long-acting solution and the preventive efficacy against induced infection of infective $3^{rd}$ stage (L3) nematode larvae 120 days after treatment were evaluated.

Ten male, healthy, ruminating Braunvieh (Brown Swiss) cattle were used in this study. They were approximately seven to eight months old and weighed 176.5 to 229.5 kg on Day—1. The cattle were worm-free as confirmed by fecal examination 15 days prior to treatment and housed under conditions which designed to preclude nematode infection.

Five replicates of two cattle each were formed based on decreasing Day—1 body weights. Within replicates, cattle were randomly allocated to Treatment Group 1 or 2: Group 1—vehicle (control) at 1 mL/50 kg body weight; Group 2—moxidectin 5% w/v LAI solution at 1 mL/50 kg body weight (1.0 mg/kg). Treatments were administered once by subcutaneous injection on Day 0 in front of the right shoulder.

Blood samples were collected from all animals and plasma recovered on Days—6, 0 (prior to treatment) and then on Days 1, 2, 3, 4, 5, 6, 7, 14 and weekly thereafter until Day 140 and on Day 148. Plasma samples were assayed for moxidectin concentration.

The injection site was grossly observed without manual manipulation on Day 0 (prior to treatment) on Day 7, and weekly thereafter until Day 140 and on Day 148.

Animals were weighed on Day-1 for allocation and dose calculation, and on Day 148.

Gastrointestinal nematode infections (10,000 infective third-stage larvae per species) were experimentally induced on Day 120: *Cooperia oncophora/surnabada, C. punctata, Ostertagia ostertagi/lyrata*, and *Trichostrongylus axei*.

Injection site reactions, non-heat swellings were observed in three of the vehicle (control) and in all five moxidectin LAI treated animals at seven days after treatment. However, all reactions resolved within four weeks and from Day 28 on, no reaction was observed in any animal.

Moxidectin LAI treatment led to a very high efficacy (>99%) against *O. ostertagi* and a high efficacy (94%) against *T. axei* while efficacy against all three *Cooperia* species was lower than 90%.

Mean plasma concentrations of moxidectin peaked ($C_{max}$) at 18.7 ng/mL. The time to maximum plasma concentration after treatment was approximately 24 hours ($T_{max}$). This first peak was followed by a second and third peak at 11.8 and 6.22 ng/mL on Days 14 and 77, respectively. The area under the plasma concentration curve to the last time point observed ($AUC_{0-last}$(ng·day)/mL) was 735 (last collection on Day 148).

Figure 6:
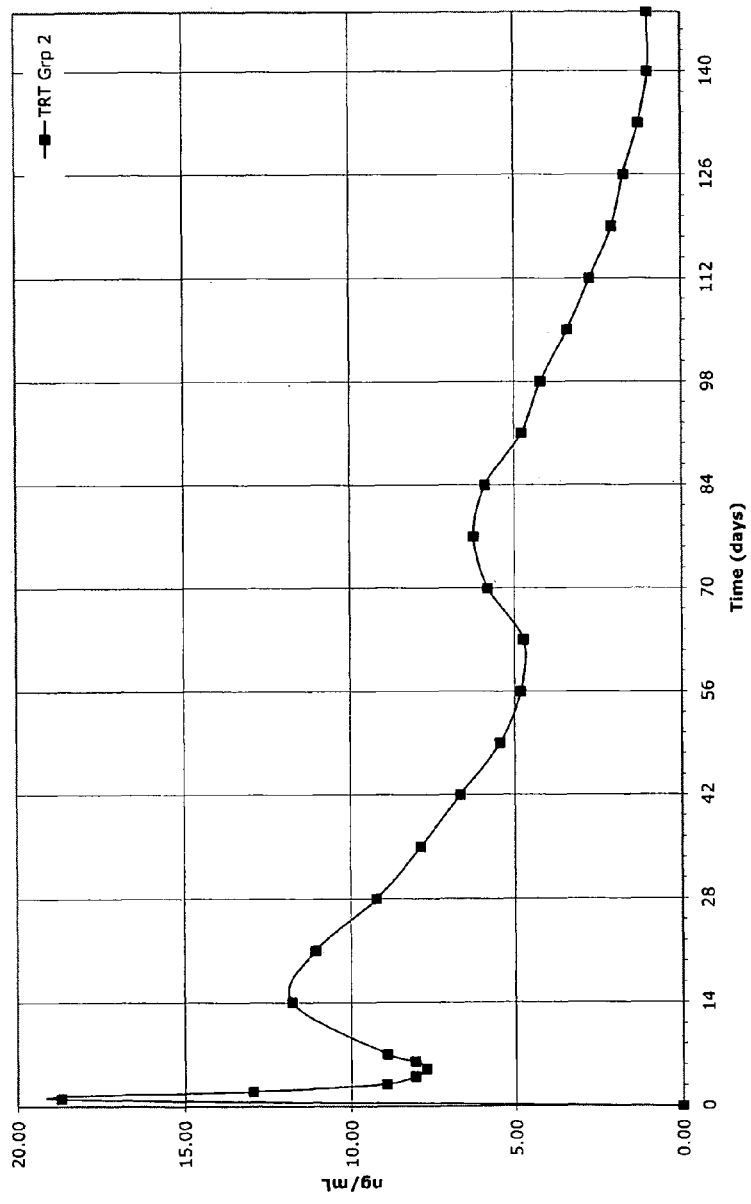
FIG. 6 shows the plasma depletion of moxidectin after injection.

All calves accepted the treatment well. No health problems were observed. The results of this test are displayed in FIG. 6.

Example 5

Study of Eprinomectin Plasma Concentration in Pigs Using Long Acting Injectable Formulations of the Invention Ten crossbred pigs were used in a study to determine the plasma profile for eprinomectin in long-acting injectable solutions. The ten pigs were ranked from highest to lowest *Strongylid* egg count in feces collected on Day—4. The three animals with the highest egg count formed Replicate 1, the next three highest formed Replicate 2 and the next three formed Replicate 3. Pigs were randomly allocated to treatment group within replicate. On Day—57 all pigs were orally inoculated with 3,000 infective Trichuris suis ova and on Day 0 were orally inoculated with 15,000 infective *Oesophagostumum* spp. $L_3$.

On Day 0:
(1) Pigs in Treatment Group 1 were untreated and served as controls;
(2) Pigs in Treatment Group 2 were administered a 5% w/v solution of eprinomectin in a 5% w/v PLGA 6535 low IV polymer contained in a triacetin/glycerol formal solvent at a 1:1 ratio. The dose was administered at 1.5 mg/kg b.w.;
(3) Pigs in Treatment Group 3 were administered a 5% w/v solution of eprinomectin in a 5% w/v ZEIN 6000 polymer contained in a triacetin/glycerol formal solvent at a 2:8 ratio.

The dose was administered at 1.5 mg/kg b.w.
Treatments were administered subcutaneously in the neck. Blood samples were collected from Treatment Group 2 and 3 pigs on Days 3, 7, 14, 28, 42, 56 and 63 and from Treatment Group 2 only on Days 70, 77 and 84. Drug concentration of eprinomectin in the plasma was measured by high performance liquid chromatography (HPLC). Pigs in Treatment Groups 1 and 3 were necropsied on Day 63 and pigs in Group 2 were necropsied on Day 84. Injection sites were examined at necropsy and the small and large intestines of each pig were examined for nematodes.
Plasma values are listed in Tables 2. Fecal egg count is listed in Table 3. Worm count data is listed in Table 4.
Treatment Group 1=Unmedicated control
Treatment Group 2=50 mg/mL dosed at 1.5 mg/kg
Treatment Group 3=50 mg/mL dosed at 1.5 mg/kg

TABLE 2

Plasma Concentration Data # of days after orally inoculated with 15,000 infective *Oesophagostumum* spp. $L_3$ and treatment with long acting injectable formulation containing eprinomectin (concentration in ng/mL)

| | 3 | 7 | 14 | 28 | 42 | 56 | 63 | 70 | 77 | 84 |
|---|---|---|---|---|---|---|---|---|---|---|
| Treatment Group 2 Animal ID | | | | | | | | | | |
| 156 | 15.1 | 11.0 | 5.6 | 4.9 | 6.8 | 3.4 | 1.8 | 0.9 | <0.5 | <0.5 |
| 160 | 18.3 | 13.8 | 8.0 | 3.2 | 3.3 | 2.9 | 1.8 | 1.2 | <0.5 | <0.5 |
| 154 | 17.3 | 10.1 | 3.7 | 2.0 | 3.6 | 3.3 | 2.3 | 1.3 | <0.5 | <0.5 |
| 163 | 16.3 | 9.8 | 6.0 | 2.6 | 3.8 | 2.9 | 2.7 | 1.8 | <0.75 | <0.75 |
| Average | 16.8 | 11.2 | 5.8 | 3.2 | 4.4 | 3.1 | 2.2 | 1.3 | | |
| Treatment Group 3 Animal ID | | | | | | | | | | |
| 161 | 19.3 | 14.3 | 7.6 | 3.6 | 1.9 | <0.5 | <0.5 | NS | NS | NS |
| 155 | 17.2 | 9.3 | 6.2 | 2.3 | 1.7 | <0.5 | <0.5 | NS | NS | NS |
| 153 | 17.6 | 13.6 | 5.6 | 1.6 | 0.8 | <0.75 | <0.5 | NS | NS | NS |
| Average | 18.0 | 12.4 | 6.5 | 2.5 | 1.5 | | | | | |

NS = not sampled;
LOD = 0.5 ng/mL;
LOQ = 0.75 ng/mL

TABLE 3

Endoparasite counts

| Animal ID | Treatment Group | Ascaris suum | Oesophagostomum spp. | Trichuris spp. |
|---|---|---|---|---|
| 157 | 1 | 18 | 4310 | 0 |
| 162 | 1 | 0 | 2780 | 0 |
| 158 | 1 | 19 | 2830 | 0 |
| 156 | 2 | 0 | 0 | 0 |
| 160 | 2 | 0 | 0 | 0 |
| 154 | 2 | 0 | 0 | 0 |
| 163 | 2 | 0 | 0 | 0 |
| 161 | 3 | 0 | 10 | 0 |
| 155 | 3 | 0 | 10 | 0 |
| 153 | 3 | 0 | 20 | 0 |

TABLE 3-continued

Example 6

Study of Eprinomectin Plasma Concentration in Sheep Using Long Acting Injectable Formulations of the Invention A study was conducted to determine the curative endoparasitic efficacy of a long-acting injectable formulation of eprinomectin administered subcutaneously at 1 mg/kg against macrocyclic lactone-resistant (ML-resistant) strains of *Haemonchus contortus* and *Ostertagia circumcincta*. Twelve, healthy, female Merino sheep aged between 18 and 24 months, weighing between 35.5 and 45 kg on Day—1 were used. The sheep were drenched with fenbendazole combined with levamisole orally at least twice the recommended dose rate on Day—50, and were worm-free before commencement of the study based on faecal nematode egg counts from faecal samples taken on Day—31. Nematode infections were induced on Day—28 with approximately 3,000 *Haemonchus contortus* (ML-Resistant), 8,000 *Ostertagia circumcincta* (moderately ML-resistant) and 6,000 *Trichostrongylus colubriformis* (ML-susceptible) per head. The study animals were ranked by decreasing Day—1 body weights and allocated consecutively to six replicates of two animals each. Within replicates, one animal was randomly allocated to each treatment group. Replicates were randomly allocated to pens. Treatment groups were as follows: Treatment Group 1—untreated control or Treatment Group 2—eprinomectin given subcutaneously at a dose rate of 1 mg/kg, once on Day 0. The sheep were held in outdoor pens by replicate under conditions that precluded unintentional nematode infection. Sheep were weighed on Days—50,-29,-1 and 29. Injection sites were observed on Day 0 before treatment and then daily for reactions from Day 1 to 7. Faeces were collected on Day 29 for individual nematode egg counts and larval cultures by treatment group. The animals were euthanised and necropsied by replicate on Day 29 for total worm counts.

Sheep treated with eprinomectin long-acting injection at 1 mg/kg subcutaneously had significantly (p<0.01) fewer of *O. circumcincta* and *T. colubriformis* than the control with reductions of 100.0%.

Figure 7:
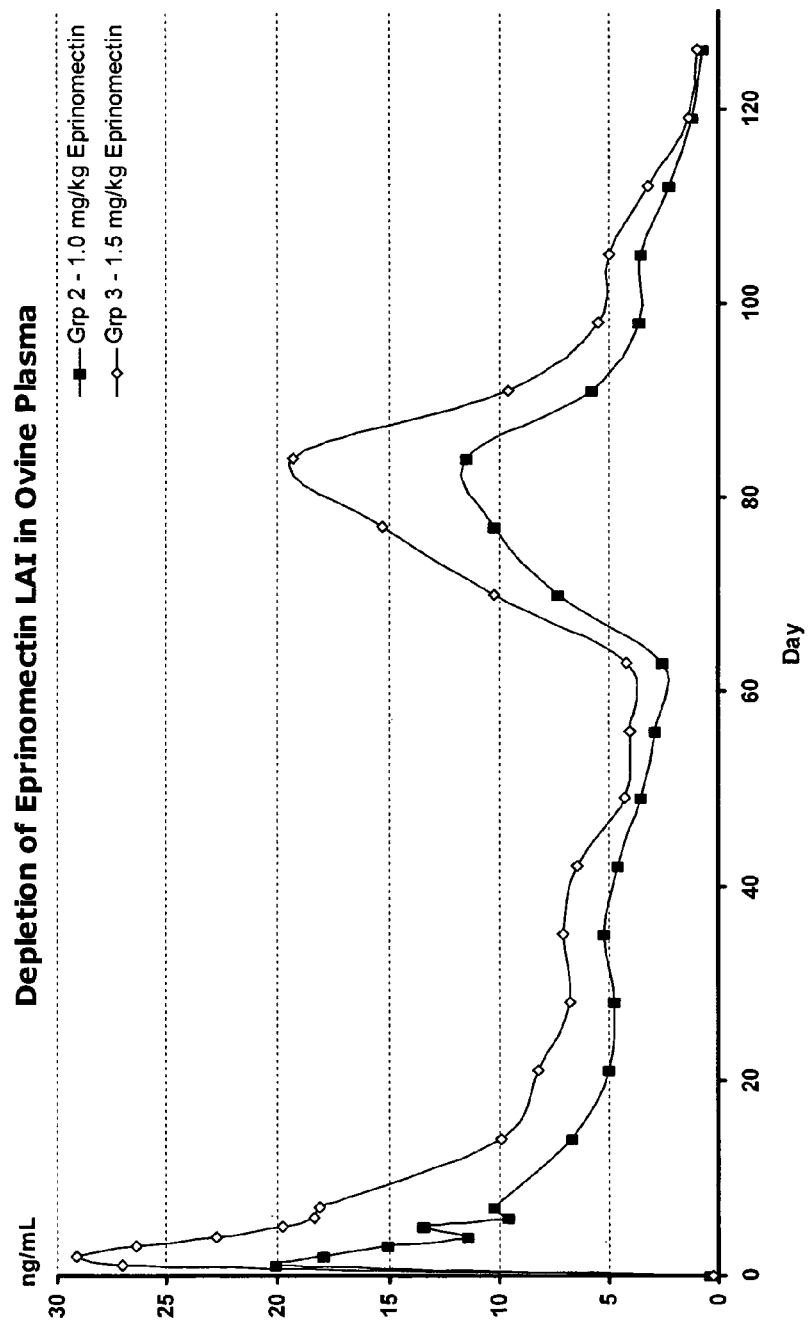
FIG. 7 shows the plasma depletion of eprinomectin in sheep after injection.

These results indicate that eprinomectin long-acting injection had a high level of curative efficacy against an ML-susceptible strain of *T. colubriformis*, and a moderately ML-resistant strain of *O. circumcincta*. However, the poor takes of the ML-resistant *H. contortus* in untreated controls makes a definitive assessment of the variable activity of eprinomectin long-acting injection observed in treated sheep against this strain, difficult. The treatment was well accepted. See FIG. 7 for graphical representation of plasma concentration.

TABLE 4

Summary of Parasite Count Data

| Parasite | Untreated Control GM[1] | Eprinomectin at 1 mg/kg subcutaneous | | |
|---|---|---|---|---|
| | | GM | Eff[2] | Prob[3] |
| Ostertagia circumcincta (ML-R) | 413.2 | 0.0 | 100.0 | <0.01 |
| Trichostrongylus colubriformis (ML-S) | 3351.7 | 0.0 | 100.0 | <0.01 |

[1]Geometric mean (GM), based on transformation to ln (count + 1): 6 animals per treatment
[2]Percent efficacy (Eff)
[3]Probability values (Prob) from Wilcoxon rank sum test comparing active treatment to control
[4]Not significant (ns) at α = 0.05
Efficacies of 90% or greater with significant differences in bold Example 7

Figure 8:
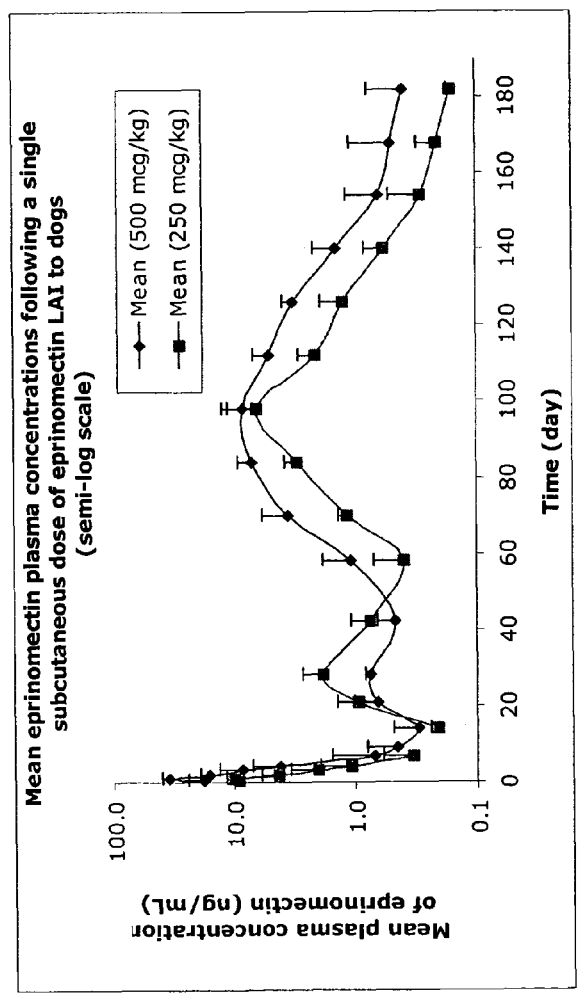
FIG. 8 shows the plasma depletion of eprinomectin in dogs after injection.

Study of Eprinomectin Plasma Concentration in Dogs After Injecting Long Acting Injectable Formulations A study was conducted to evaluate plasma levels of eprinomectin following treatment of dogs with eprinomectin long acting formulation of the invention at a dose of 200 or 500 mcg/kg. Formulations were 0.5-1.0% w/v eprinomectin, 30% v/v NMP, 5% w/v PLGA (90:10 ratio of polylactide:glycolide), 0.02% w/v BHT, and q.s. to 100% v/v triacetin. As can be seen from FIG. 8, effective plasma concentrations are detected in the dogs for at least 180 days.

Example 8

PLGA Formulations Containing Ivermectin for Testing with Dogs

The long acting injectable formulations of the invention can also be applied to dogs. Advantageously, certain embodiments of these formulations include:

(1) 85% PL: 15% GA (5% w/w PLGA) in 5% NMP: 95% triacetin, 0.6% w/w ivermectin;
(2) 85% PL: 15% GA (5% w/w PLGA) in 5% Ethylacetamide: 95% triacetin, 0.6% w/w ivermectin;
(3) 90% PL: 10% GA (5% w/w PLGA) in 5% NMP: 95% triacetin, 0.6% w/w ivermectin;
(4) 90% PL: 10% GA (5% w/w PLGA) in 5% Ethylacetamide: 95% triacetin, 0.6% w/w ivermectin;
(5) 85% PL: 15% GA (5% w/w PLGA) in 5% NMP: 95% triacetin, 1.0% w/w ivermectin;
(6) 85% PL: 15% GA (5% w/w PLGA) in 5% Ethylacetamide: 95% triacetin, 1.0% w/w ivermectin;
(7) 85% PL: 15% GA (10% w/w PLGA) in 5% Ethylacetamide: 95% triacetin, 1.0% w/w ivermectin;
(8) 85% PL: 15% GA (5% w/w PLGA) in 30% NMP: 70% triacetin, 0.6% w/w ivermectin;
(9) 85% PL: 15% GA (5% w/w PLGA) in 30% Ethylacetamide: 70% triacetin, 0.6% w/w ivermectin;
(10) 90% PL: 10% GA (5% w/w PLGA) in 30% NMP: 70% triacetin, 0.6% w/w ivermectin;
(11) 90% PL: 10% GA (5% w/w PLGA) in 30% Dimethylacetamide: 70% triacetin, 0.6% w/w ivermectin;

Other advantageous embodiments using dimethylacetamide include:

| Ivermectin (w/v) | Polymer (PL:GA) | DMAC:TA | Dose volume (mL/20 kg) | Dose Level (mcg/kg) |
|---|---|---|---|---|
| 0.6 | 90:10 | 30:70 | 1 | 300 |
| 0.6 | 90:10 | 50:50 | 1 | 300 |
| 1 | 90:10 | 30:70 | 1 | 500 |
| 1 | 90:10 | 50:50 | 1 | 500 |
| 0.6 | 95:5 | 30:70 | 1 | 300 |
| 0.6 | 95:5 | 50:50 | 1 | 300 |
| 1 | 95:5 | 30:70 | 1 | 500 |
| 1 | 95:5 | 50:50 | 1 | 500 |

Even more advantageously, 250 mL solutions based on the above described embodiments can be prepared:

Dog Formulation #1

| Ingredient | % | Amount for 250 mL solution |
|---|---|---|
| Ivermectin | 0.60 w/v | 1.64 g |
| PLGA (85:15) | 5.00 w/v | 12.50 g |
| BHT | 0.02 w/v | 0.05 g |
| Pharmasolve (NMP) | 5.00 v/v | 12.50 mL |
| Triacetin | q.s to 100% v/v | q.s. ad 250 mL |

Dog Formulation #2

| Ingredient | % | Amount for 250 mL solution |
|---|---|---|
| Ivermectin | 0.60 w/v | 1.64 g |
| PLGA (85:15) | 5.00 w/v | 12.50 g |
| BHT | 0.02 w/v | 0.05 g |
| Ethyl acetate | 5.00 v/v | 12.50 mL |
| Triacetin | q.s to 100% v/v | q.s. ad 250 mL |

Dog Formulation #3

| Ingredient | % | Amount for 250 mL solution |
|---|---|---|
| Ivermectin | 0.60 w/v | 1.64 g |
| PLGA (90:10) | 5.00 w/v | 12.50 g |
| BHT | 0.02 w/v | 0.05 g |
| Pharmasolve (NMP) | 5.00 v/v | 12.50 mL |
| Triacetin | q.s to 100% v/v | q.s. ad 250 mL |

Dog Formulation #4

| Ingredient | % | Amount for 250 mL solution |
|---|---|---|
| Ivermectin | 0.60 w/v | 1.65 g |
| PLGA (90:10) | 5.00 w/v | 12.50 g |
| BHT | 0.02 w/v | 0.05 g |
| Ethyl acetate | 5.00 v/v | 12.50 mL |
| Triacetin | q.s to 100% v/v | q.s. ad 250 mL |

Dog Formulation #5

| Ingredient | % | Amount for 250 mL solution |
|---|---|---|
| Ivermectin | 1.00 w/v | 2.75 g |
| PLGA (85:15) | 5.00 w/v | 12.50 g |
| BHT | 0.02 w/v | 0.05 g |
| Pharmasolve (NMP) | 5.00 v/v | 12.50 mL |
| Triacetin | q.s to 100% v/v | q.s. ad 250 mL |

Dog Formulation #6

| Ingredient | % | Amount for 250 mL solution |
|---|---|---|
| Ivermectin | 1.00 w/v | 2.75 g |
| PLGA (85:15) | 5.00 w/v | 12.50 g |
| BHT | 0.02 w/v | 0.05 g |
| Ethyl acetate | 5.00 v/v | 12.50 mL |
| Triacetin | q.s to 100% v/v | q.s. ad 250 mL |

Dog Formulation #7

| Ingredient | % | Amount for 250 mL solution |
|---|---|---|
| Ivermectin | 1.00 w/v | 2.75 g |
| PLGA (85:15) | 10.00 w/v | 25.00 g |
| BHT | 0.02 w/v | 0.05 g |
| Ethyl acetate | 5.00 v/v | 12.50 mL |
| Triacetin | q.s to 100% v/v | q.s. ad 250 mL |

Dog Formulation #8

| Ingredient | % | Amount for 250 mL solution |
|---|---|---|
| Ivermectin | 0.60 w/v | 1.65 g |
| PLGA (85:15) | 5.00 w/v | 12.50 g |
| BHT | 0.02 w/v | 0.05 g |
| Pharmasolve (NMP) | 30.00 v/v | 75.00 mL |
| Triacetin | q.s to 100% v/v | q.s. ad 250 mL |

Dog Formulation #9

| Ingredient | % | Amount for 250 mL solution |
|---|---|---|
| Ivermectin | 0.60 w/v | 1.65 g |
| PLGA (85:15) | 5.00 w/v | 12.50 g |
| BHT | 0.02 w/v | 0.05 g |
| Ethyl acetate | 30.00 v/v | 75.00 mL |
| Triacetin | q.s to 100% v/v | q.s. ad 250 mL |

Figure 9:
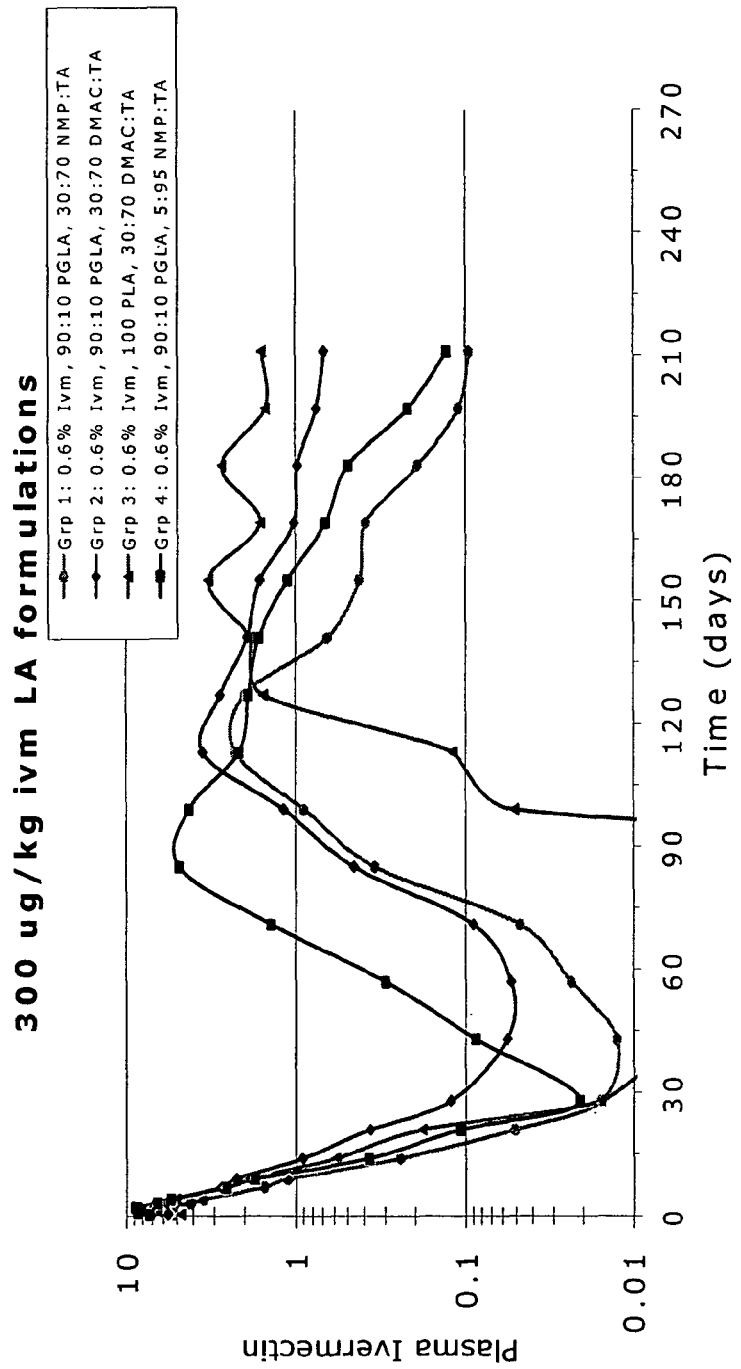
FIG. 9 shows the plasma depletion of ivermectin in dogs after injection.

See FIG. 9 for graphical representation of data.

Example 9

LAI Formulations with Alternate Solvents

| | Ingredient | % |
|---|---|---|
| Formulation 1 | Eprinomectin | 5.00 w/v |
| | PLGA (75:25) | 5.00 w/v |
| | BHT | 0.02 w/v |
| | Triacetin | q.s to 100% v/v |
| Formulation 2 | Eprinomectin | 5.00 w/v |
| | PLGA (75:25) | 5.00 w/v |
| | BHT | 0.02 w/v |
| | Solketal | 30.00 w/v |
| | Triacetin | q.s to 100% v/v |
| Formulation 3 | Eprinomectin | 5.00 w/v |
| | PLGA (75:25) | 5.00 w/v |
| | BHT | 0.02 w/v |
| | Propylene carbonate | 30.00 w/v |
| | Triacetin | q.s to 100% v/v |
| Formulation 4 | Eprinomectin | 5.00 w/v |
| | PLGA (75:25) | 5.00 w/v |
| | BHT | 0.02 w/v |
| | Ethyl lactate | 30.00 w/v |
| | Triacetin | q.s to 100% v/v |

Example 10

LAI Formulations in Combination with Other Actives (Clorsulon)

| | Ingredient | % |
|---|---|---|
| Formulation 1 | Eprinomectin | 5.00 w/v |
| | Clorsulon | 10.00 w/v |
| | PLGA (75:25) | 5.00 w/v |
| | BHT | 0.02 w/v |
| | Solketal | 30.00 w/v |
| | Triacetin | q.s to 100% v/v |
| Formulation 2 | Eprinomectin | 5.00 w/v |
| | Clorsulon | 10.00 w/v |
| | PLGA (75:25) | 5.00 w/v |
| | BHT | 0.02 w/v |
| | Propylene carbonate | 30.00 w/v |
| | Triacetin | q.s to 100% v/v |
| Formulation 3 | Ivermectin | 1.00 w/v |
| | Chlorsulon | 10.00 w/v |
| | PLGA (75:25) | 5.00 w/v |
| | BHT | 0.02 w/v |
| | Solketal | 30.00% w/v |
| | Triacetin | q.s to 100% v/v |
| Formulation 4 | Ivermectin | 1.00 w/v |
| | Chlorsulon | 10.00 w/v |
| | PLGA (75:25) | 5.00 w/v |
| | BHT | 0.02 w/v |
| | Propylene carbonate | 30.00% w/v |
| | Triacetin | q.s to 100% v/v |

The long acting injectable (LAI) formulations of the invention in the examples above all included PLGA and a solvent and were able deliver their respective active agents (eprinomectin, ivermectin, moxidectin and emamectin) for long periods of time. The formulations of the invention can carry multiple actives and were shown to be useful in multiple species in the examples provided above (cattle, sheep, pigs and dogs). In addition, the examples further show that the LAI formulations of the invention can be administered in the shoulder, in the neck or caudal to the ear with similar duration (see Examples 1-4) and surprisingly that efficacy of the formulations of the invention are effective against endoparasitic strains which are resistant to conventional formulations (e.g. macrocyclic lactones (see Example 5).

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A liquid long acting injectable formulation for combating ectoparasites and/or endoparasites in a mammal comprising:
   (a) a therapeutically effective amount of bioactive agent which comprises a combination of at least one of abamectin, doramectin, emamectin, eprinomectin, ivermectin, latidectin, lepimectin, selamectin, milbemectin, milbemycin D, milbemycin oxime, or moxidectin and clorsulon;
   (b) a subcutaneously volatile solvent or mixture of subcutaneously volatile solvent;
   (c) a biologically acceptable polymer, wherein the biologically acceptable polymer is present in an amount of up to 10%, and wherein said polymer is poly(lactic-co-glycolic) acid copolymer;
   (d) optionally, at least one pharmaceutically acceptable additive, excipient or mixtures thereof; and
   (e) an antioxidant.

2. The formulation of claim 1, wherein:
the subcutaneously volatile solvent is selected from the group consisting of alcohols, aldehydes, ketones, ethers, esters, amides and mixtures thereof.

3. The formulation of claim 2, wherein:
   (a) the bioactive agent is a combination of at least one of doramectin, emamectin, eprinomectin or moxidectin and clorsulon;
   (b) the subcutaneously volatile solvent is selected from the group consisting of ethanol, 1-propanol, 2-propanol, 1-butanol, 2-butanol, 1-pentanol, 2-pentanol, 3-pentanol, propylene glycol, PEG 200, PEG 300, PEG 400, diethylene glycol ethyl ether, isopropylidene glycerol, dimethyl isosorbide, propylene carbonate, glycerol, acetone, N-methyl-pyrrolidone, N-pyrrolidone, methylethylketone (MEK), dimethylsulfoxide (DMSO), 1-dodecylazacycloheptane, dipropyleneglycol methyl ether, methyl acetate, ethyl acetate, ethyl lactate, dimethylformamide, N,N-diethyl-m-toluamide, dimethylacetamide, ethylacetamide, tetrahydrofuran, caprolactam, decylmethylsulfoxide, triacetin, solketal, propylene carbonate, ethyl lactate and mixtures thereof.

4. The formulation of claim 1, wherein:
   (a) the bioactive agent is selected from the group consisting of emamectin, eprinomectin, ivermectin, or moxidectin and clorsulon;
   (b) the subcutaneously volatile solvent is selected from the group consisting of glycerol formal, N-methylpyrrolidone (NMP), triacetin, dimethylacetamide, ethylacetamide, ethyl acetate, solketal, propylene carbonate, ethyl lactate and mixtures thereof, and
   (d) the antioxidant is butylated hydroxytoluene.

5. A method of combating ectoparasites and/or endoparasites in a mammal comprising parenteral administration of a therapeutically effective amount of the formulation of claim 1 to a mammal in need thereof.

6. The method of claim 5, wherein the endoparasite is selected from the group consisting of *Ancylostoma, Anecator, Ascaris, Capillaria, Cooperia, Dirofilaria, Dictyocaulus, Echinococcus, Fasciola, Haemonchus, Oesophagostomum, Ostertagia, Toxocara, Strongyloides, Toxascaris, Trichinella, Trichuris, Trichostrongylus* and mixtures thereof.

7. The method of claim 5, wherein the ectoparasite is selected from the group consisting of *Ctenocephalides, Rhipicephalus, Dermacentor, Ixodes, Boophilus, Ambylomma, Hyalomma, Sarcoptes, Psoroptes, Otodectes, Chorioptes, Hypoderma, Damalinia, Linognathus, Hematopinus, Solenoptes* and mixtures thereof.

8. The method of claim 5, wherein the site of injection on the mammal is subcutaneous and is selected from the group consisting of the ear; base of the ear between the shoulder, in the neck; and the shoulder.

9. The method of claim 5, wherein the endoparasite is a helminth selected from the group consisting of *Ostertagia, Haemonchus*, and mixtures thereof wherein said helminth is resistant to macrolide antibiotics when not administered by the method of claim 5.

10. A liquid long acting injectable formulation for combating ectoparasites and/or endoparasites in a mammal comprising:
    (a) a therapeutically effective amount of a combination of at least one of eprinomectin, ivermectin, moxidectin or emamectin with clorsulon;
    (b) N-methyl pyrrolidone;
    (c) 5% w/v poly(lactic-coglycolic acid); and
    (d) butylated hydroxytoluene.

11. The composition of claim 10, wherein said clorsulon is present in an amount of about 10% (w/v).

12. The composition of claim 1, wherein said clorsulon is present in an amount of about 10% (w/v).

* * * * *